US012036085B2

(12) United States Patent
Oren-Artzi et al.

(10) Patent No.: US 12,036,085 B2
(45) Date of Patent: Jul. 16, 2024

(54) SYSTEMS AND METHODS FOR REMOTE DENTAL MONITORING

(71) Applicant: Get-Grin Inc., Airmont, NY (US)

(72) Inventors: Pamela Sharon Oren-Artzi, Airmont, NY (US); Alon Luis Lipnik, Airmont, NY (US); Adam Benjamin Schulhof, Airmont, NY (US); David Ben-Ari, Airmont, NY (US)

(73) Assignee: GET-GRIN INC., Airmont, NY (US)

( * ) Notice: Subject to any disclaimer, the term of this patent is extended or adjusted under 35 U.S.C. 154(b) by 0 days.

(21) Appl. No.: 18/057,095

(22) Filed: Nov. 18, 2022

(65) Prior Publication Data
US 2023/0149129 A1 May 18, 2023

Related U.S. Application Data

(63) Continuation of application No. PCT/US2021/032932, filed on May 18, 2021.
(Continued)

(51) Int. Cl.
A61C 7/00 (2006.01)
A61B 1/24 (2006.01)
(Continued)

(52) U.S. Cl.
CPC ............. A61C 7/002 (2013.01); A61B 1/24 (2013.01); A61B 5/0088 (2013.01);
(Continued)

(58) Field of Classification Search
CPC ...... A61C 7/002; A61C 9/0053; G16H 80/00; A61B 1/24; A61B 5/0088; A61B 5/6898;
(Continued)

(56) References Cited

U.S. PATENT DOCUMENTS 6,402,707 B1 6/2002 Ernst, II et al.
7,717,708 B2 5/2010 Sachdeva et al.
(Continued)

FOREIGN PATENT DOCUMENTS

WO WO-2018085718 A2 5/2018
WO WO-2019215129 A1 11/2019
(Continued)

OTHER PUBLICATIONS

El Kattan et al. A New Horizontal Plane of the Head. Open Access Maced J Med Sci. May 20, 2018; 6(5):767-771. Retrieved Mar. 1, 2023 at URL: https://oamjms.eu/index.php/mjms/article/view/oamjms. 2018.172/2103.
(Continued)

Primary Examiner — Timothy A Musselman
(74) Attorney, Agent, or Firm — Wilson Sonsini Goodrich & Rosati

(57) ABSTRACT

The present disclosure provides systems and methods for remote dental monitoring. In an aspect, the present disclosure provides a computer-implemented method for remote dental monitoring. The method may comprise (a) providing a patient portal for one or more patients to remotely communicate with a caregiver, wherein the patient portal comprises a graphical user interface that is configured to aid the one or more patients in capturing one or more dental scans, wherein the one or more dental scans comprise (i) one or more intraoral videos and (ii) a plurality of images derived from the one or more intraoral videos; and (b) providing the one or more dental scans to the caregiver for an assessment of a dental condition based on the one or more dental scans.

17 Claims, 38 Drawing Sheets

Related U.S. Application Data

(60) Provisional application No. 63/027,883, filed on May 20, 2020, provisional application No. 63/144,088, filed on Feb. 1, 2021.

(51) Int. Cl.
  *A61B 5/00* (2006.01)
  *A61C 9/00* (2006.01)
  *G09B 19/00* (2006.01)
  *G16H 80/00* (2018.01)

(52) U.S. Cl.
  CPC .......... *A61B 5/6898* (2013.01); *A61B 5/7425* (2013.01); *A61B 5/7465* (2013.01); *A61C 9/0053* (2013.01); *G09B 19/003* (2013.01); *G16H 80/00* (2018.01)

(58) Field of Classification Search
  CPC .... A61B 5/7425; A61B 5/7465; G09B 19/003
  See application file for complete search history.

(56) References Cited

U.S. PATENT DOCUMENTS

| | | |
|---|---|---|
| 10,123,706 B2 | 11/2018 | Elbaz et al. |
| 11,392,210 B2 | 7/2022 | Sabina et al. |
| 11,638,636 B2 | 5/2023 | Oren-Artzi et al. |
| 2008/0172386 A1 | 7/2008 | Ammar et al. |
| 2008/0286712 A1 | 11/2008 | Imgrund et al. |
| 2009/0076321 A1 | 3/2009 | Suyama et al. |
| 2014/0272764 A1 | 9/2014 | Miller et al. |
| 2016/0373155 A1 | 12/2016 | O'Neill et al. |
| 2018/0263730 A1 | 9/2018 | Sirovskiy et al. |
| 2018/0368943 A1 | 12/2018 | Katzman et al. |
| 2019/0200903 A1 | 7/2019 | Watson |
| 2019/0254790 A1 | 8/2019 | Lancelle et al. |
| 2019/0313963 A1 | 10/2019 | Hillen |
| 2019/0328489 A1 | 10/2019 | Capron-Richard et al. |
| 2020/0000551 A1 | 1/2020 | Li et al. |
| 2020/0138518 A1* | 5/2020 | Lang .................... A61B 5/05 |
| 2020/0143541 A1 | 5/2020 | Wang et al. |
| 2020/0305808 A1 | 10/2020 | Ezhov et al. |
| 2020/0349356 A1 | 11/2020 | Matias et al. |
| 2020/0404243 A1 | 12/2020 | Saphier et al. |
| 2021/0220086 A1* | 7/2021 | German ................ A61B 5/4547 |
| 2021/0282634 A1 | 9/2021 | Oren-Artzi et al. |
| 2021/0377374 A1* | 12/2021 | Peterson ............ A61B 1/00128 |
| 2023/0149135 A1 | 5/2023 | Lipnik et al. |

FOREIGN PATENT DOCUMENTS

| | | |
|---|---|---|
| WO | WO-2021130582 A1 | 7/2021 |
| WO | WO-2021236616 A1 | 11/2021 |
| WO | WO-2022020267 A1 | 1/2022 |
| WO | WO-2023278354 A1 | 1/2023 |
| WO | WO-2023009763 A1 | 2/2023 |
| WO | WO-2023009764 A1 | 2/2023 |
| WO | WO-2023009859 A2 | 2/2023 |

OTHER PUBLICATIONS

PCT/US2021/032932 International Search Report and Written Opinion dated Sep. 9, 2021.
PCT/US2021/042247 International Search Report and Written Opinion dated Nov. 3, 2021.
PCT/US2022/035176 International Search Report and Written Opinion dated Sep. 15, 2022.
PCT/US2022/038737 International Search Report and Written Opinion dated Dec. 19, 2022.
PCT/US2022/038943 International Search Report and Written Opinion dated Feb. 16, 2023.
Prados-Privado et al. A Convolutional Neural Network for Automatic Tooth Numbering in Panoramic Images. BioMed Research International, vol. 2021, Article ID 3625386, 7 pages. Published Dec. 14, 2021.
Co-pending U.S. Appl. No. 18/397,182, inventors Lipnik; Alon Luis et al., filed Dec. 27, 2023, Mar. 14, 2024.
Co-pending U.S. Appl. No. 18/424,169, inventors Lipnik; Alon Luis et al., filed Jan. 26, 2024.
Co-pending U.S. Appl. No. 18/424,237, inventors Raz; Carmi et al., filed Jan. 26, 2024.
EP21809886.1 Extended European Search Report dated May 8, 2014.

* cited by examiner

SYSTEMS AND METHODS FOR REMOTE DENTAL MONITORING

CROSS-REFERENCE

This application is a continuation of International Patent Application No. PCT/US21/32932 filed on May 18, 2021, which claims priority to U.S. Provisional Patent Application No. 63/027,883 filed on May 20, 2020 and U.S. Provisional Patent Application No. 63/144,088 filed on Feb. 1, 2021, each of which is incorporated herein by reference in its entirety for all purposes.

BACKGROUND

Dental professionals and orthodontists may treat and monitor a patient's dental condition based on in-person visits. Treatment and monitoring of a patient's dental condition may require a patient to schedule multiple in-person visits to a dentist or orthodontist. The quality of treatment and the accuracy of monitoring may vary depending on how often and how consistently a patient sees a dentist or orthodontist. In some cases, suboptimal treatment outcomes may result if a patient is unable or unwilling to schedule regular visits to a dentist or orthodontist.

SUMMARY

Recognized herein is a need for remote dental monitoring solutions to allow dental patients to receive high quality dental care, without requiring a dental professional to be physically present with the patient. Some dental professionals and orthodontists may use conventional teledentistry solutions to accommodate patients' needs and schedules. However, such conventional teledentistry solutions may not provide adequate levels of supervision. Further, such conventional teledentistry solutions may be limited by an inaccurate or insufficient monitoring of patients' dental condition based on one or more photos taken by the patients, if the photos do not adequately capture various intraoral features of interest.

The present disclosure provides systems and methods for intraoral imaging to enhance remote dental monitoring capabilities. The systems and methods disclosed herein may provide a convenient solution and user experience for dental patients to capture one or more intraoral images or videos using a mobile device such as a smartphone. The systems and methods disclosed herein may allow patients to capture improved self-scans of full dental arches using a mobile application installed on their mobile device, and may provide automated, personalized guidance to the patients to allow the patients to capture high quality self-scans that are useful for dentists to monitor and track the patients' progress during a dental treatment. The systems and methods disclosed herein may enhance a patient's ability to assess or evaluate their dental condition based on one or more full arch self-scans, and may provide dentists and orthodontists with a detailed analysis of the patient's dental condition based on one or more full arch scans captured remotely by the patient.

The systems and methods of the present disclosure may also be used to provide dental patients with an intuitive, user-friendly interface for remote dental scanning without requiring assistance from a dentist or a dental assistant. The intuitive, user-friendly interface may be provided as part of a software application that provides step-by-step guidance for dental patients to acquire images and videos of one or more intraoral regions that are of sufficient quality and detail to enable dentists to accurately assess a need for dental treatment, a need to update or modify a dental treatment, or a patient's compliance with the dental treatment. The software applications disclosed herein may also permit dentists to request and view high quality images or videos of a patient's teeth so that the dentist can continue to monitor the patient's teeth or treatment progress without being physically present and without having to provide personalized or customized instructions for how to acquire the intraoral images or videos. The software applications disclosed herein may also provide a convenient way for dentists to monitor dental patients and dental treatment progress when the dental patients are unable to physically travel to the dentist for treatment or treatment monitoring (e.g., due to shelter-in-place orders). The systems and methods of the present disclosure may provide dentists and dental patients with the ability to continue treatment or treatment monitoring while practicing social distancing, thereby reducing a possibility of the transmission of infectious diseases.

In an aspect, the present disclosure provides a computer-implemented method for remote dental monitoring. The method comprises (a) providing a patient portal for one or more patients to remotely communicate with a caregiver, wherein the patient portal comprises a graphical user interface that is configured to aid the one or more patients in capturing one or more dental scans, wherein the one or more dental scans comprise (i) one or more intraoral videos and (ii) a plurality of images derived from the one or more intraoral videos; and (b) providing the one or more dental scans to the caregiver for an assessment of a dental condition based on the one or more dental scans. In some embodiments, the assessment of the dental condition comprises one or more annotations to the one or more dental scans. In some embodiments, the assessment of the dental condition comprises at least one of audio commentary and visual commentary to the one or more dental scans. In some embodiments, the assessment of the dental condition comprises an audio or video recording of the caregiver providing commentary or annotations to the one or more dental scans.

In some embodiments, the caregiver may comprise a dentist, an orthodontist, an oral surgeon, a dental staff practitioner, or an individual having one or more dental specialties. In some embodiments, the plurality of images may be derived from one or more frames of the one or more intraoral videos. The plurality of images may comprise a plurality of intraoral images of one or more intraoral regions of the patient. The one or more dental scans may further comprise one or more selfie videos or selfie images of the one or more patients.

In some embodiments, the graphical user interface may be configured to provide visual, textual and/or audio guidance to aid the one or more patients in capturing the one or more dental scans. The graphical user interface may be configured to provide the one or more patients with a patient-specific treatment timeline comprising one or more customized treatment milestones and dates. The graphical user interface may be configured to prompt the one or more patients to capture the one or more dental scans on or before the one or more treatment milestones and dates. The patient-specific timeline may be configured to display a plurality of dental scans captured by a patient for each treatment milestone and date. The plurality of dental scans may be arranged in chronological order.

In some embodiments, the one or more dental scans may be captured using one or more cameras of a mobile device. The mobile device may be coupled to an intraoral adapter comprising a viewing channel for capturing the one or more dental scans. The viewing channel may comprise a hexagonal or a polygonal rounded cross-sectional shape. The one or more dental scans may comprise a dental imaging region in which one or more dental features or intraoral regions are visible or displayed after the one or more dental scans are captured. The dental imaging region may be in a shape that is configured to enable the one or more patients to capture one or more intraoral videos or intraoral images of a molar region while minimizing a movement of an image capture device that is used to capture the one or more dental scans, so as to provide stabilization to enable consistent image alignment for processing. In some cases, the shape may be a hexagon or a rounded polygon.

In some embodiments, the visual guidance may comprise one or more visual markings or guides for alignment with one or more teeth of the one or more patients. The one or more dental scans may be automatically captured when the one or more teeth of the one or more patients are aligned with the one or more visual markings or guides. The visual guidance may comprise one or more visual markings or guides for the one or more patients to adjust a position or an orientation of a camera of a mobile device to align one or more teeth with the one or more visual markings or guides. The textual guidance may comprise textual instructions for the one or more patients to attach a mobile device to an intraoral adapter and to move the mobile device or the intraoral adapter to capture the one or more dental scans. The textual instructions may be configured to instruct the one or more patients to adjust a position or an orientation of the mobile device or the intraoral adapter to capture the one or more dental scans.

In some embodiments, the visual, textual and/or audio guidance may comprise one or more video tutorials containing examples to guide the one or more patients for capturing the one or more dental scans. The visual, textual and/or audio guidance may comprise one or more software tools to assist the one or more patients in performing the one or more dental scans. The one or more software tools may comprise a scan module that is configured to detect an orientation of a mobile device used to capture the one or more dental scans. The scan module may be configured to (1) pause the capture of the one or more dental scans, and/or (2) generate a visual or audio prompt to the one or more patients, upon detecting that the mobile device is not positioned in a predefined orientation for capturing the one or more dental scans. In some cases, the predefined orientation may be a landscape orientation of the mobile device. In some embodiments, the visual, textual and/or audio guidance may comprise a set of instructions to the one or more patients for retaking the one or more dental scans.

In some embodiments, the treatment milestones and dates may be influenced in part by one or more factors including an aligner replacement schedule. The aligner replacement schedule may be associated with a plurality of trays containing a set of aligners that are designed to be worn by the one or more patients in a sequence. The plurality of trays may be provided to the one or more patients in a pre-locked state. Unlocking of one or more of the trays may be contingent upon the one or more patients successfully completing one or more of the customized treatment milestones. In some cases, a code may be generated upon successful completion of a particular treatment milestone by the one or more patients, wherein the code is useable to unlock a tray containing a new aligner to be worn by the one or more patients. In some cases, the code may comprise an alphanumeric code, a barcode, or a QR code.

In some embodiments, the patient portal may comprise a chat user interface that is configured to facilitate remote communication between the patient and the dentist. The chat user interface may be configured to display the one or more dental scans captured by the one or more patients to enable viewing and access by the caregiver and the one or more patients while chatting.

In another aspect, a computer-implemented method for remote dental monitoring is provided. The method comprises providing a caregiver portal for one or more caregivers to remotely monitor a dental condition of one or more patients, wherein the caregiver portal comprises a graphical user interface that is configured to display one or more dental scans captured by the one or more patients, wherein the one or more dental scans comprise (i) one or more intraoral videos and (ii) a plurality of images derived from the one or more intraoral videos.

In some embodiments, the caregiver portal may comprise a task board interface configured to provide caregivers with information on one or more tasks associated with incoming patients, current patients, and preparation for dental treatment of the incoming patients or the current patients. The caregiver portal may comprise a chat user interface that is configured to facilitate remote communication between the caregiver and the patient. The chat user interface may be configured to display the one or more dental scans captured by the one or more patients to enable viewing and access by the caregiver and the one or more patients while chatting. The chat interface may be configured to display the one or more dental scans according to a patient-specific treatment timeline comprising one or more treatment milestone and dates.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
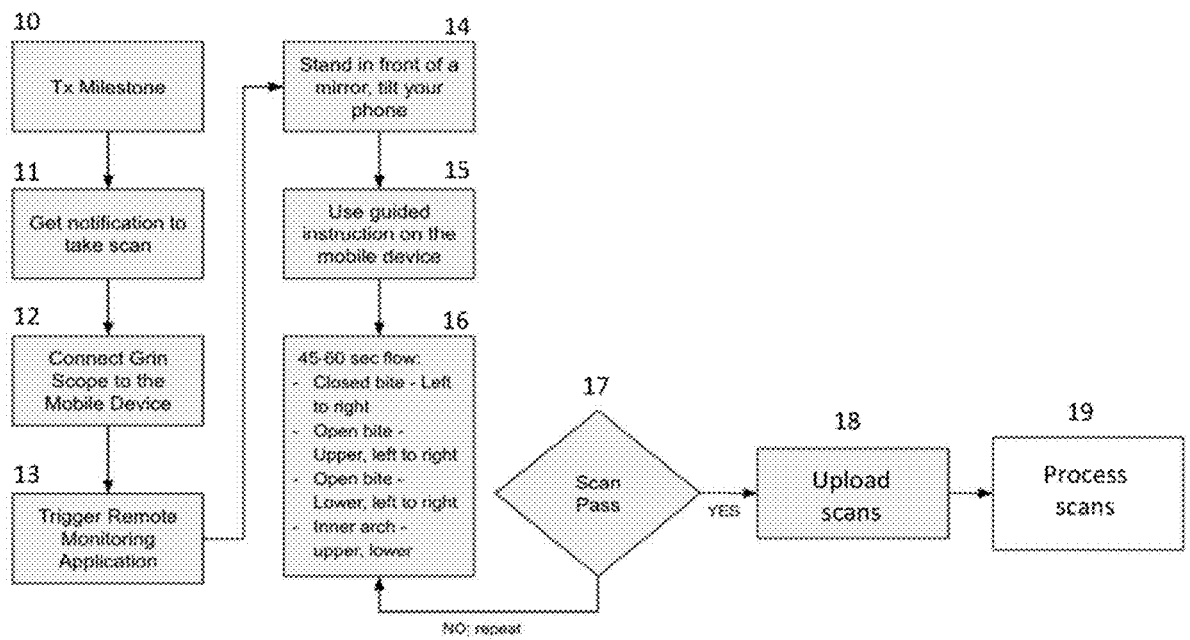
FIG. 1 schematically illustrates a method for capturing intraoral images or videos using a software application, in accordance with some embodiments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "real-time," as used herein, generally refers to a simultaneous or substantially simultaneous occurrence of a first event or action with respect to an occurrence of a second event or action. A real-time action or event may be performed within a response time of less than one or more of the following: ten seconds, five seconds, one second, a tenth of a second, a hundredth of a second, a millisecond, or less relative to at least another event or action. A real-time action may be performed by one or more computer processors.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The terms "a," "an," and "the," as used herein, generally refer to singular and plural references unless the context clearly dictates otherwise.

Overview

In an aspect, the present disclosure provides systems and method for remote dental monitoring. The present disclosure provides systems and methods for intraoral imaging to enhance remote dental monitoring capabilities. The systems and methods disclosed herein may provide a convenient solution and user experience for dental patients to capture one or more intraoral images or videos using a mobile device such as a smartphone. The systems and methods disclosed herein may allow patients to capture improved self-scans of a full dental arch using a mobile application installed on their mobile device, and may provide automated, personalized guidance to the patients to allow the patients to capture high quality self-scans that are useful for dentists to monitor and track the patient's progress during a dental treatment. The systems and methods disclosed herein may enhance a patient's ability to assess or evaluate their dental condition based on one or more full arch self-scans, and may provide dentists and orthodontists with a detailed analysis of the patient's dental condition based on one or more full arch scans captured remotely by the patient.

The systems and methods of the present disclosure may also be used to provide dental patients with an intuitive, user-friendly interface for remote dental scanning without requiring assistance from a dentist or a dental assistant. The intuitive, user-friendly interface may be provided as part of a software application that provides step-by-step guidance for dental patients to acquire images and videos of one or more intraoral regions that are of sufficient quality and detail to enable dentists to accurately assess a need for dental treatment, a change in a dental treatment, or a patient's compliance with the dental treatment. The software applications disclosed herein may permit dentists to request and view high quality images or videos of a patient's teeth so that the dentist can continue to monitor the patient's teeth or treatment progress without being physically present and without having to provide personalized or customized instructions for how to acquire the intraoral images or videos. The software applications of the present disclosure may further provide a convenient way for dentists to monitor dental patients and dental treatment progress when the dental patients are unable to physically travel to the dentist for treatment or treatment monitoring (e.g., due to shelter-in-place orders). The systems and methods of the present disclosure may provide dentists and dental patients with the ability to continue treatment or treatment monitoring while practicing social distancing, thereby reducing a possibility of the transmission of infectious diseases.

In an aspect, the present disclosure provides systems and methods for remote monitoring. The systems and methods of the present disclosure may be implemented using a software application that is configured to enable a dental patient to capture images and/or videos of intraoral regions. The software application may be used by a user or a subject (e.g., a dental patient) in conjunction with a mobile device to remotely monitor a dental anatomy or a dental condition of the subject. A dental anatomy may comprise one or more dental structures of the patient, including one or more tooth structures or dental arches of the subject. The dental condition may comprise a development, a growth, a movement, an appearance, a condition, a physical arrangement, a position, and/or an orientation of the subject's teeth. In some cases, the dental condition may comprise a functional aspect of the user's teeth, such as how two or more teeth contact each other, how the teeth move relative to each other, or how the teeth move over a period of time.

The software application may be used to enable remote dental monitoring. As used herein, remote monitoring may refer to monitoring a dental anatomy or a dental condition of a patient that is performed at one or more locations remote from the patient. For example, a dentist or a medical specialist may monitor the dental anatomy or dental condition in a first location that is different than a second location where the patient is located. The first location and the second location may be separated by a distance spanning at least about 1 meter, 1 kilometer, 10 kilometers, 100 kilometers, 1000 kilometers, or more.

The remote monitoring may be performed by assessing a dental anatomy or a dental condition of the subject using one or more intraoral images or videos captured by the subject when the patient is located remotely from the dentist or a dental office. In some cases, the remote monitoring may be performed in real-time such that a dentist is able to assess the dental anatomy or the dental condition when a subject uses a mobile device to acquire one or more intraoral images or videos of one or more intraoral regions of interest in the patient's mouth. The remote monitoring may be performed using equipment, hardware, and/or software that is not physically located at a dental office.

The software application may be configured to run on a mobile device. The mobile device may comprise a smartphone, a tablet, a laptop, or any suitable computing device that may be used by a patient to capture one or more dental scans. The software application may be installed on a mobile device of a patient undergoing a dental treatment or who will be undergoing a dental treatment. The software application may be a patient-side software application.

In some cases, the patient-side software application may be used in a compatible manner with a practitioner-side software application that is accessible by a caregiver. The patient-side software application and the practitioner-side software application may enable real-time communication and sharing of images, videos, or data between one or more patients and one or more caregivers. The one or more caregivers may comprise, for example, a dentist, an orthodontist, an oral surgeon, individuals having one or more dental specialties, or a dental staff practitioner. The practitioner-side software application may be implemented using a computer, a mobile device, or a server (e.g., a cloud server). The practitioner-side software application may be accessed through a computer, a mobile device, or a web interface.

Patient Portal

The software application may be configured to implement a computer-implemented method for remote dental monitoring. The method may comprise (a) providing a patient portal for one or more patients to remotely communicate with a caregiver. The patient portal may comprise a graphical user interface that is configured to aid the one or more patients in capturing one or more dental scans. In some cases, the one or more dental scans may comprise one or more intraoral images or videos. In other cases, the one or more dental scans may comprise one or more intraoral videos and/or one or more images derived from the one or more intraoral videos. The method may further comprise (b) providing the one or more dental scans to a caregiver for an assessment of a dental condition based on the one or more dental scans.

The patient portal may be an interactive visual interface that can be displayed on a mobile device of a patient. The patient portal may be navigated, manipulated, and/or updated using one or more user gestures or inputs (e.g., taps, swipes, etc.) that are provided to the mobile device. The patient may use the patient portal to remotely communicate with a caregiver who wishes to monitor a dental condition of the patient.

The patient portal may comprise a chat user interface that is configured to facilitate remote communication between the patient and the dentist. The chat user interface may provide a chat window for the patient to send text, images, videos, and/or data to the dentist. The chat user interface can provide a virtual chat room for the patient to communicate with the dentist, dental staff or assistants, receptionist, etc. Likewise, the dentist or any of the dental staff/assistants may use the chat user interface to send text, images, videos, and/or data to the patient.

The chat user interface may be configured to display one or more dental scans captured by a patient. The patient may use the chat user interface to send one or more dental scans captured by the patient to the dentist. In such instances, the chat user interface may enable the dentist to view and/or access the one or more dental scans while communicating with the patient (e.g., through an exchange of text messages, images, videos, data, etc.) The chat user interface may also permit the patient and the dentist to discuss the patient's dental treatment, dental condition, and/or any specific visual features in the one or more dental scans, without having to navigate to a separate user interface to view (i) the patient's dental scans or (ii) any images, videos, or data associated with the patient's dental treatment or dental condition. In addition to improving ease of use, the functionality and layout of the chat user interface may enhance efficient communication between the patient and dentist so that the dentist can remotely provide a quick and convenient assessment of the patient's dental condition or dental treatment.

The patient portal may be configured to enable the patient to capture one or more dental scans. The dental scans may be of a dental feature of the patient. The dental feature may comprise, for example, the patient's teeth, gums, dental arches, and/or any treatment devices (e.g., braces or aligners) in contact and/or proximal to the user's teeth, gums, or dental arches.

The one or more dental scans may comprise one or more intraoral images of a dental feature of the patient. The one or more dental scans may comprise one or more intraoral videos of a dental feature of the patient. In some cases, the intraoral images may be derived from the one or more intraoral videos. The intraoral images may comprise one or more still images associated with one or more frames of the intraoral videos.

The dental scans may comprise a plurality of intraoral images or a plurality of intraoral videos of one or more intraoral regions within the patient's mouth. The one or more intraoral regions may comprise one or more dental features as described above.

In some cases, the one or more dental scans may further comprise one or more selfie videos or selfie images of the one or more patients. The selfie videos or selfie images may be used to visualize an appearance or a change of an appearance of the user's smile, jaw structure, cheeks, mouth, teeth, dental arches, etc. before, during, and/or after a dental treatment.

Capturing Scans

In some cases, the patient portal may comprise a graphical user interface that is configured to aid the one or more patients in capturing one or more dental scans. In some cases, the graphical user interface may comprise an image capture user interface which may be launched through the chat user interface described herein. The chat user interface may include a camera icon that may be pressed or tapped by a patient to launch the image capture user interface to capture one or more dental scans.

The image capture user interface may be displayed on a screen of the patient's mobile device. The patient may attach a mobile device to a compatible intraoral adapter to capture the dental scans. The intraoral adapter may provide an imaging channel for the mobile device to capture the dental scans. The screen of the mobile device may be oriented away from the patient when coupled to the intraoral adapter so that a rear camera of the mobile device may be used to capture the dental scans. In such cases, the patient may face a mirror and use a reflected mirror image of the patient to view and manipulate the image capture user interface displayed on the screen of the patient's mobile device.

The image capture user interface may show an imaging window that is configured to display a live, real-time visual representation of an imaging region that is visible to the one or more cameras of the mobile device. The patient may tap an image capture button to capture one or more images, videos, or dental scans corresponding to the live, real-time visual representation of the imaging region displayed in the imaging window. The image capture user interface may further comprise an image gallery button that may be pressed by the patient to access images, videos, or dental scans already captured by the patient using the mobile device. The image capture user interface may further comprise a camera swap button that may be pressed by the patient to switch between one or more cameras (e.g., a front camera or a rear camera) of the patient's mobile device. The images, videos, and/or dental scans captured using the one or more cameras of the mobile device may be shared with or sent to a dentist through the chat user interface described herein.

The one or more dental scans may be captured using one or more cameras of a mobile device. In some cases, the mobile device may be coupled to a compatible intraoral adapter comprising a viewing channel for capturing the one or more dental scans. The intraoral adapter may be configured to provide an imaging region for the one or more cameras of the mobile device. One or more of the patient's dental features or intraoral regions may be viewable within the imaging region, which may be defined by a size and/or a shape of the intraoral adapter. In some cases, the viewing channel of the intraoral adapter may comprise a hexagonal or a polygonal rounded cross-sectional shape. In some cases, the shape and/or size of the viewing channel may provide or define one or more main imaging regions for imaging a first intraoral region and one or more peripheral imaging regions for imaging a second intraoral region (e.g., the patient's molar regions). Using a compatible intraoral adapter may provide multiple benefits, such as consistently defining an appropriate or suitable dental imaging region and standardizing a distance between the cameras of the patient's mobile device and the one or more dental features the patient wishes to image.

Figure 3:
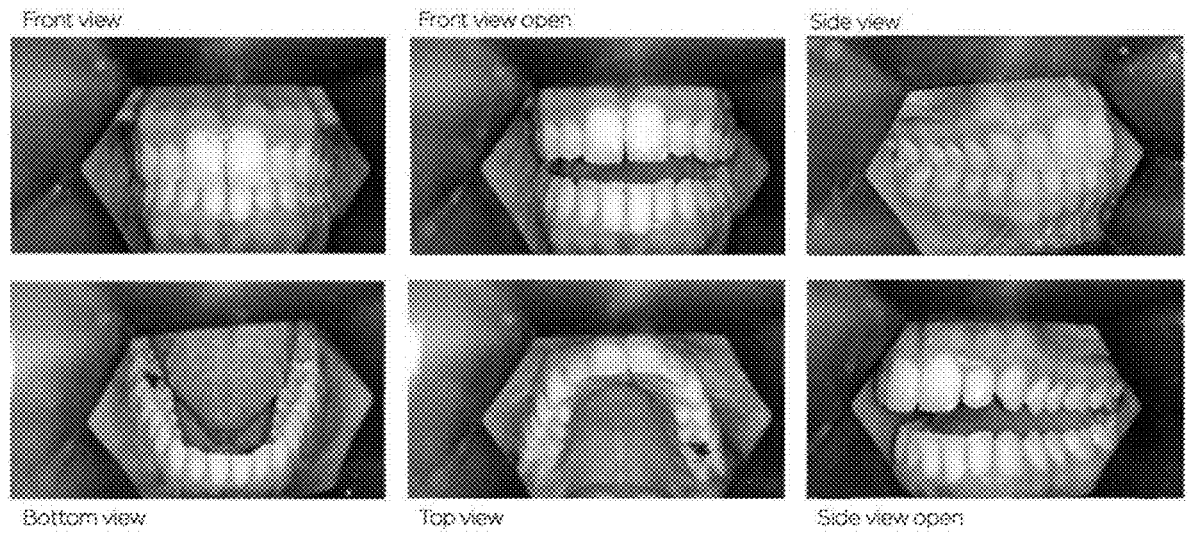
FIG. 3 schematically illustrates a plurality of intraoral images captured using the software application, in accordance with some embodiments.

In some cases, the dental imaging region may comprise a shape that is configured to enable the patient to capture one or more intraoral videos or intraoral images of a molar region while minimizing a movement of the mobile device and the intraoral adapter that is used to capture the one or more dental scans, so as to provide stabilization to enable consistent image alignment for (e.g., for subsequent image processing). The shape of the dental imaging region may be a circle, an ellipse, an oval, or a polygon with three or more side. In some cases, the dental imaging region may be in the shape of a hexagon or a rounded polygon. In such cases, the dental scans captured using the mobile device and the intraoral adapter may be framed within a hexagonal shape as shown in FIG. 3.

In some cases, the intraoral adapter may further comprise one or more sensors configured to automatically detect when a patient's smartphone camera and the intraoral adapter are optically aligned to capture one or more dental scans. In some cases, the intraoral adapter may be configured to permit dynamic adjustment of lighting, illumination, brightness, contrast, and/or any other imaging conditions so that the patient may take suitable dental scans using the intraoral adapter and the patient's mobile device. In some cases, the intraoral adapter may be configured to permit the patient to take a plurality of images with different lighting conditions or illumination conditions to reveal certain characteristics that are only apparent or visible under such conditions. The plurality of images may comprise one or more bright-field images and/or one or more dark-field images. In some cases, the intraoral adapter may be configured to adjust an amount of light that is transmitted through the intraoral adapter (e.g., from a camera flash of the patient's mobile device).

Visual/Textual/Audio Guidance

In some cases, the graphical user interface and/or the image capture user interface of the patient-side software application may be configured to provide the patient with visual, textual, and/or audio guidance to aid the patient in capturing the one or more dental scans. The visual and/or textual guidance may be visible on the display of the patient's mobile device and may be viewed by the patient using a reflected mirror image that is visible to the patient when the patient is positioned in front of a mirror or another reflective surface. The patient-side software application may be configured to provide audio guidance, for example a voice over to assist the patient with the proper capture of the dental scans. The audio guidance may be transmitted via a speaker on the patient's mobile device. The visual, textual, and/or audio guidance may include one or more video tutorials containing examples to guide the one or more patients.

In some cases, the textual guidance may comprise textual instructions for the patient to attach a mobile device to a compatible intraoral adapter, to place the intraoral scope over the patient's mouth and face a mirror, to bite down and/or smile, to turn the patient's head relative to the intraoral scope, to open the patient's mouth for imaging of top or bottom dental arches, and/or to move the mobile device or the intraoral adapter relative to one or more dental features or intraoral regions of the patient to capture the one or more dental scans. In some cases, the textual instructions may be configured to instruct the patient to adjust a position or an orientation of the mobile device or the intraoral adapter relative to the one or more dental features or intraoral regions to capture the dental scans. In some cases, the textual instructions may instruct the patient to adjust a position or an orientation of the patient's head, face, or mouth relative to the mobile device or the intraoral adapter to capture the one or more dental scans.

In some cases, the visual, textual, and/or audio guidance may include one or more software tools to assist the one or more patients in performing a scan. The software tools may include a scan module that is configured to detect an orientation of a mobile device used to capture the one or more dental scans. The scan module can be configured to (1) pause the capture of the one or more dental scans, and/or (2) generate a textual or audio prompt to the one or more patients, if the mobile device is not positioned in a predefined orientation (e.g. landscape orientation) for capturing the one or more dental scans.

In some cases, the visual guidance may provide a visualization of how to attach the mobile device to the intraoral adapter. In some cases, the visual guidance may comprise one or more visual markings or guides for the one or more patients to adjust a position or an orientation of a camera of a mobile device to align one or more teeth with the one or more visual markings or guides. The one or more visual markings or guides may be used at least in part to perform an alignment between the camera of the mobile device and one or more dental features or intraoral regions of the patient. The visual markings or guides may comprise one or more dots, lines, shapes (e.g., regular shapes, irregular shapes, and/or amorphous shapes), or other two-dimensional or three-dimensional features that the patient may use to align a camera of the mobile device with one or more dental features or intraoral regions of the patient. In some cases, the visual marking or guides may be sized and/or shaped to approximate a profile, a shape, or an arrangement of the patient's teeth or dental arches. The patient-side software application may be configured to automatically capture the one or more dental scans when one or more dental features or intraoral regions of the patient are aligned with the one or more visual markings or guides, or a subset thereof.

After one or more intraoral images or videos are captured, the patient-side software application may provide visual and/or textual instructions for the patient to capture one or more selfie images or videos. The selfie images or videos may be captured using the mobile device of the patient. The mobile device may not or need not be coupled to the intraoral adapter to capture the selfie images. The visual and/or textual instructions may instruct the patient to relax the patient's lips, to smile, and to take a picture of the patient's face. The visual and/or textual instructions may instruct the patient to turn the patient's face (e.g., up, down, left, and/or right) or to face forward towards a camera of the mobile device.

After the intraoral images/videos and the selfie images/videos are captured, the patient-side software application may be configured to present the patient with an option to retake the images and/or videos if needed or desired. As an example, the visual, textual, and/or audio guidance disclosed elsewhere herein may include instructions to the patient for retaking the one or more dental scans. In some cases, the patient-side software application may be configured to present the patient with an option to send the images and/or videos to a dentist via the chat user interface.

Patient Timeline/Milestones

In some cases, the graphical user interface of the patient-side software application may be configured to provide the patient with a patient-specific treatment timeline associated with a dental treatment of the patient. In some cases, the dental treatment may comprise changing a layout, an arrangement, a position, or an orientation of the patient's teeth using aligners or braces. The patient-specific treatment timeline may comprise one or more treatment milestones and dates. The treatment milestones and dates may comprise dates on which the dentist wishes to check up on the patient or to assess a progress of the dental treatment. The patient-specific treatment timeline may comprise at least 1, 2, 3, 4, 5, 6, 7, 8, 9, 10, or more treatment milestones and dates.

In some cases, the graphical user interface of the patient-side software application may be configured to prompt the patient to capture the one or more dental scans on or before the one or more treatment milestones and dates. In some cases, the patient-specific timeline may be configured to display a plurality of dental scans captured by the patient for each treatment milestone and date.

The patient-specific treatment timeline may be updated based on the dental scans captured by the patient using a mobile device and/or the intraoral adapter. The treatment milestones and dates may likewise be updated based on the dental scans captured by the patient. In some cases, the patient-specific treatment timeline and/or the treatment milestones and dates may be updated based on one or more trends associated with the dental scans captured by the patient over a period of time.

In some cases, the patient-specific treatment timeline may be a predicted patient-specific treatment timeline that is generated based on one or more predictions of how long a dental treatment may take, or an estimated progress of the dental treatment over a period of time based on patient-specific parameters. The patient-specific parameters may be associated with a dental condition of the patient or one or more physical characteristics (e.g., layout, arrangement, relative position, and/or relative orientation) of the patient's dental features. The predicted patient-specific treatment timeline may be updated based on one or more dental scans captured by the patient using the systems and methods disclosed herein. The predicted patient-specific treatment timeline may be updated based on one or more dental scans captured by the patient for one or more treatment milestones and dates associated with the predicted patient-specific treatment timeline.

In any of the embodiments described herein, the treatment timeline associated with a patient's dental treatment may be automatically and dynamically changed, modified, or updated in real-time based on the dental scans captured by the patient. Likewise, the steps or the milestones or dates associated with the patient's dental treatment may be automatically and dynamically changed, modified, or updated in real-time based on the dental scans captured by the patient. In some cases, new steps and/or milestones may be added to the dental treatment plan to influence or change the course of treatment. The new steps and/or milestones may be inserted chronologically between two or more existing steps or milestones. In some cases, one or more existing milestones associated with the patient's dental treatment can be changed, deleted, or moved anywhere along the patient's treatment timeline. In some cases, one or more portions of the treatment timeline may be expedited or compressed if the dental scans suggest that the patient is showing faster than expected progress and/or a favorable response during the course of treatment.

In any of the embodiments described herein, the treatment timeline may graphically display changes in the treatment timeline or treatment milestones to the patient once the patient's dental scans are assessed or analyzed. The treatment timeline may be configured to keep the user informed as to the current stage of the dental treatment, what steps or milestones the patient has completed, and what steps or milestones the patient can expect next or in the near future. The patient-side software application may be configured to permit the patient to click on any point or milestone along the treatment timeline, to scroll along the treatment timeline and view previously captured dental scans, to annotate one or more portions of the treatment timeline with questions or comments for the dentist or caregiver to address. The patient-side software application may be further configured to send alerts or notifications to the patient in real-time about changes in the patient's treatment timeline or changes to one or more milestones associated with the patient's treatment timeline.

In some cases, the dental scans may be visually analyzed by the dentist or a dental assistant to determine a dental condition of the patient. In some cases, the dental scans may be visually analyzed by the dentist or a dental assistant to assess the patient's progress in relation to a dental treatment plan or a predicted patient-specific treatment timeline associated with the dental treatment plan. The dentist may use the visual analysis of the dental scans to update or change the dental treatment plan, the patient-specific treatment timeline, or one or more treatment milestones and dates associated with the patient-specific treatment timeline. In other cases, the dental scans may be analyzed and/or processed using an image processing algorithm.

In some cases, the treatment milestones and dates may be influenced in part by one or more factors, such as an aligner replacement schedule. The aligner replacement schedule may be associated with a plurality of trays containing a set of aligners that are designed to be worn by the patient in sequence. In some cases, the plurality of trays may be provided to the patient in a pre-locked state. When the patient successfully completes a particular treatment milestone at a certain point, the patient portal described herein can generate a code to the patient. The code may be specific or unique to a tray containing a prescribed aligner for achieving the next treatment milestone. The patient can then use the code to unlock the tray to access the new aligner.

The code for unlocking aligner trays may comprise an alphanumeric code, a barcode, or a QR code. Other examples of codes that may include Aztec, ColorCode, Color Construct Code, CrontoSign, CyberCode, d-touch, DataGlyphs, Data Matrix, Datastrip Code, Digimarc Barcode, DotCode, DWCode, EZcode, High Capacity Color Barcode, Han Xin Barcode, HueCode, InterCode, MaxiCode, Mobile Multi-Colored Composite (MMCC), NexCode, PDF417, Qode, ShotCode, Snapcode, SPARQCode, VOICEYE, a modification thereof, or a combination thereof. The code can be of any image format (e.g. EPS or SVG vector graphs, PNG, GIF, or JPEG raster graphics format).

Controlling access to the aligner trays can help to increase patient compliance and improve quality of care. The trays can be numbered or marked sequentially to allow the user to progress to the next tray upon completion of the previous step/milestone. In some cases, the trays need not be numbered or marked sequentially, and the patient portal may reveal the next tray only upon successful completion of a required action by the patient (for example, completion of a milestone scan), or based on a message from the patient to the caregiver, or based on an authorization from the caregiver permitting the patient to access the next tray. The examples above can help to streamline caregiver supervision of the treatment progress and effectiveness, and also increase patient compliance with the treatment process.

Improved User Interaction

In some cases, the patient-side software application may be configured to incentivize and/or improve patient interaction and engagement. For example, the patient-side software application may be configured to implement one or more aspects of gamification by providing incentives, rewards, or points to a patient when the patient successfully completes and uploads one or more dental scans. In some cases, the incentives may be provided by dental insurance companies (e.g., reductions in insurance payout costs for patients who maintain good dental health or comply with their dental treatment plan). The patient-side software application may also be configured to provide positive reinforcement by visually showing the patient's progress with respect to a dental treatment plan (e.g. 80% towards end goal or completion of treatment). The patient-side software application may be configured to encourage users to collect regular scans, may give personalized messages to the patient to encourage regular scanning, and may provide reminders and alerts to the patient's smartphone for upcoming treatment milestones and dates. In some cases, the patient-side software application may be configured to graphically display a scoreboard corresponding to the patient's completion of one or more steps in a dental treatment plan or a completion of one or more milestone scans.

Image Processing

In some cases, the dental scans captured using the patient's mobile device may be provided to an image processing algorithm. The image processing algorithm may be implemented on the mobile device on which the software application is installed. The image processing algorithm may be implemented on a remote server or a cloud server. The image processing algorithm may be implemented on a computing device that is accessible by the caregiver. The image processing algorithm may be configured to process one or more intraoral images and/or one or more intraoral videos.

The image processing algorithm may be configured to (i) process the dental scans captured using the camera of the mobile device, and (ii) determine a dental condition of the subject based at least in part on the processed dental scans. The dental condition may comprise (i) a movement of one or more teeth of the subject, (ii) an accumulation of plaque on the one or more teeth of the subject, (iii) a change in a color or a structure of the one or more teeth of the subject, (iv) a change in a color or a structure of a tissue adjacent to the one or more teeth of the subject, and/or (v) a presence or lack of presence of one or more cavities. In some embodiments, the image processing algorithm may be configured to process the dental scans to (i) predict a movement of one or more teeth of the subject, (ii) identify enamel wear patterns, (iii) create or modify a dental treatment plan, or (iv) generate or update a medical record associated with the dental condition of the subject. Processing the dental scans may comprise comparing a first set of pixel values within a dental scan to a second set of pixel values within the dental scan. The pixel values may comprise a value corresponding to a color or a brightness of one or more pixels. In some cases, processing the dental scans may comprise comparing one or more pixel values within a dental scan to a set of reference pixel values within a reference image. The set of reference pixel values may be accessed through a database that is located remote from a mobile device of the patient. In some cases, the set of reference pixel values may indicate a certain dental condition (e.g., a presence of plaque or a presence of cavities). In some cases, processing the plurality of intraoral images may comprise comparing a first dental scan to a second dental scan. Comparing a first dental scan to a second dental scan may comprise tracking a movement of one or more features that are visible within the first dental scan and the second dental scan. Comparing a first dental scan to a second dental scan may comprise tracking a change in a shape of a subject's dental arches between the first dental scan and the second dental scan. In some cases, comparing a first dental scan to a second dental scan may comprise tracking a change in one or more pixel values between the first dental scan and the second dental scan. In some cases, the first dental scan and the second dental scan may be obtained within a single scanning session. In some cases, the first dental scan may be obtained during a first scanning session (e.g., at a first treatment milestone and date) and the second dental scan may be obtained during a second scanning session that is initiated after the first scanning session (e.g., at a second treatment milestone and date).

The processed dental scans may be used to automatically update a patient's dental treatment plan, predicated treatment timeline, and/or the treatment milestones and dates associated with the patient's predicted treatment timeline. In some embodiments, the processed dental scans may be usable to generate or update a dental treatment plan. In some embodiments, the processed dental scans may be usable to track one or more changes in a dental structure or a dental condition of the patient over time. In some embodiments, the processed dental scans may be usable to assess the subject's actual progress in relation to a dental treatment plan based at least in part on a comparison of one or more changes in the dental structure or the dental condition of the subject over two or more dental scans. In some embodiments, the processed dental scans may be usable to assess the subject's actual progress in relation to a dental treatment plan based at least in part on a comparison of a planned or estimated change in the dental structure or the dental condition of the subject and an actual change in the dental structure or the dental condition of the subject.

In some cases, processing the dental scans may comprise classifying the dental scans based on the dental features present within the dental scans. In some cases, processing the dental scans may comprise classifying the dental scans based on a type of dental treatment that is being remotely monitored. The dental scans may be used to build a database of temporal and treatment-based images.

In some cases, processing the dental scans may comprise comparing the dental scans to prior scans or reference scans to determine deviations between a patient's actual and predicted treatment progress, or to determine a degree of similarity or correlation between actual and predicted treatment progress. In some cases, processing the dental scans may comprise identifying areas or sections of dental structures that deviate from predicted outcomes. The systems and methods disclosed herein may be configured to optimize, adjust, or fine tune dental treatment plans, treatment timelines, and/or treatment milestones and dates based on information or data derived from processed dental scans.

Machine Learning/Neural Networks

In some cases, the dental scans may be provided to a machine learning algorithm or one or more neural networks. The machine learning algorithm may be applied to a plurality of features extracted from or identified within the dental scans. In some embodiments, the machine learning algorithm may be, for example, an unsupervised learning algorithm, a supervised learning algorithm, or a combination thereof. The unsupervised learning algorithm may comprise or may be configured to implement, for example, clustering, hierarchical clustering, k-means, mixture models, DBSCAN, OPTICS algorithm, anomaly detection, local outlier factor, neural networks, autoencoders, deep belief nets, Hebbian learning, generative adversarial networks, self-organizing map, expectation— maximization algorithm (EM), method of moments, blind signal separation techniques, principal component analysis, independent component analysis, non-negative matrix factorization, singular value decomposition, or any combination thereof. In some embodiments, the supervised learning algorithm may comprise or may be configured to implement, for example, support vector machines, linear regression, logistic regression, linear discriminant analysis, decision trees, k-nearest neighbor algorithm, neural networks, similarity learning, or any combination thereof.

In some embodiments, the machine learning algorithm may comprise a deep neural network (DNN). The deep neural network may comprise a convolutional neural network (CNN). The CNN may be, for example, U-Net, ImageNet, LeNet-5, AlexNet, ZFNet, GoogleNet, VGGNet, ResNet18 or ResNet, etc. Other neural networks may be, for example, deep feed forward neural network, recurrent neural network, LSTM (Long Short Term Memory), GRU (Gated Recurrent Unit), Auto Encoder, variational autoencoder, adversarial autoencoder, denoising auto encoder, sparse auto encoder, boltzmann machine, RBM (Restricted BM), deep belief network, generative adversarial network (GAN), deep residual network, capsule network, or attention/transformer networks, etc. In some embodiments, the neural network may comprise neural network layers. The neural network may have at least about 2 to 1000 or more neural network layers. In some cases, the machine learning algorithm may be, for example, a random forest, a boosted decision tree, a classification tree, a regression tree, a bagging tree, a neural network, or a rotation forest.

The machine learning algorithm and/or the one or more neural networks may be configured to collect large amounts of patient dental data to train machine learning models for a more accurate prediction of a patient's treatment progress or for a more accurate prediction of one or more likely treatment outcomes for a patient's dental treatment plan. The machine learning models may be used to predict a course of treatment based on a patient's profile, dental history, treatment outcomes for similar patients, and factors such as a patient's age, gender, ethnicity, genetic profile, dietary profile, and/or existing health conditions. In some cases, the machine learning models may be used to perform feature extraction, feature identification, and/or feature classification for one or more dental features present or visible within a patient's dental scans.

The machine learning algorithm and the one or more neural networks may be configured to compile the dental scans into a dental data set. The dental data set may be generated based on a plurality of dental scans captured by a plurality of different dental patients. The dental scans may comprise intraoral images and/or intraoral videos captured from a plurality of different angles or perspectives. The machine learning algorithm and the one or more neural networks may be configured to update the dental data set with additional dental scans received by one or more dental patients. The machine learning algorithm and the one or more neural networks may use the dental data set to generate one or more dental models.

The one or more dental models may be configured to receive a set of input dental scans from a dental patient and to update, modify, or change the dental patient's treatment plan and/or treatment timeline based on the input dental scans and the dental data set. The dental data set may further comprise dental scans from patients who have similar characteristics (e.g., age, race, ethnicity, gender, treatment type, etc.) to the patient providing the input dental scans. In some cases, the dental data set may comprise dental scans from patients who have characteristics (e.g., age, race, ethnicity, gender, treatment type, etc.) that are different than those of the patient providing the input dental scans. The dental models may be configured to update, modify, or change a dental patient's treatment plan and/or treatment timeline based on the patient's input dental scans and the dental data set compiled using dental scans captured by other patients.

In some cases, the dental models may be configured to take into account a patient's latest dental scans or a patient's historical dental scans when updating, modifying, or changing a dental patient's treatment plan and/or treatment timeline. In some cases, the dental models may be configured to take into account one or more trends associated with the patient's dental scans (e.g., a movement of the patient's teeth and/or a change in a position or an orientation of the patient's teeth over time) when updating, modifying, or changing a dental patient's treatment plan and/or treatment timeline. In some cases, the dental models may be configured to compare a first dental patient's dental scans to a second dental patient's dental scans before updating, modifying, or changing the first dental patient's treatment plan and/or treatment timeline. The second dental patient's dental scans may be part of the dental data set compiled using dental scans captured by a plurality of dental patients who are not the first dental patient.

In some cases, the dental models may be configured to estimate a treatment progress for a first dental patient based on a treatment progress for a second dental patient who is undergoing or has undergone a same or similar dental treatment. In some cases, the dental models may be configured to update, modify, and/or change the first dental patient's dental treatment or treatment timeline based on a discrepancy between the estimated treatment progress and the actual treatment progress for the first dental patient. In some cases, the dental models may be used to determine whether a patient is on track with an estimated treatment progress or if the patient's dental treatment plan requires adjustments.

In some cases, the dental models may be used to simulate a dental condition or a treatment progress of a dental patient at a certain timepoint in the future based on the one or more dental scans. The timepoint may be at least about 1 day, 2 days, 3 days, 4 days, 5 days, 6 days, 1 week, 2 weeks, 3 weeks, 4 weeks, 1 month, 2 months, 3 months, 4 months, 5 months, 6 months, 7 months, 8 months, 9 months, 10 months, 11 months, 12 months, 1 year, or more from a milestone date on which the one or more dental scans are captured by the dental patient.

3D Models

In some embodiments, the system, methods, software applications and/or image processing algorithms disclosed herein may be configured to generate one or more updated three-dimensional (3D) oral models of a dental feature or dental structure of a patient. In one aspect, the present disclosure provides a method for forming the one or more updated 3D oral models. The method may comprise receiving an initial 3D oral model and a plurality of dental scans or milestone scans. The method may further comprise segmenting the initial 3D oral model based on a position and/or an orientation of one or more teeth of the patient. The method may further comprise reconstructing a rough 3D oral model based on the plurality of dental scans or milestone scans to generate a rough 3D point cloud. The method may further comprise sampling a second point cloud from the initial 3D oral model and determining a point-correspondence between at least a portion of the rough 3D point cloud and the second point cloud associated with the initial 3D oral model. The method may further comprise performing an approximate piecewise rigid registration of the initial 3D oral model to the rough 3D oral model. The method may further comprise determining one or more rigid transformation parameters based on at least a portion of the rough 3D point cloud, the second point cloud associated with the initial 3D oral model, and the point-correspondence between the point clouds. The method may further comprise applying a mesh deformation to the initial 3D oral model based on the rigid transformation parameters to generate the updated three-dimensional (3D) oral model. The updated 3D oral model may be a high-quality model that shows the patient's teeth in their updated positions and orientations.

In some embodiments, the initial 3D oral model may be generated by and/or received from a clinical dental scanner. The initial 3D oral model may comprise one or more triangle meshes representing a surface of a dental feature or an intraoral region of the patient. In some embodiments, the segmentation may comprise one or more visual annotations for one or more portions of the initial 3D oral model. In some embodiments, the plurality of dental scans or milestone scans may be captured using a mobile phone of a patient. The mobile phone may be coupled to a compatible intraoral adapter as described elsewhere herein. In some embodiments, the point-correspondence may comprise an association between reference points in the segmented initial 3D oral model and reference points in the rough 3D oral model. The reference points may correspond to points of the point clouds associated with the initial 3D oral model and the rough 3D oral model. The reference points may correspond to a gum portion and/or a tooth portion of the initial 3D oral model and the rough 3D oral model. In some embodiments, the reference points may be associated with a fixed region (e.g. a gum portion of the patient) that serves as an anchor point for determining the rigid transformation parameters. Such anchor points may place the rough 3D reconstruction and the sampled point cloud from the initial 3D oral model in a same frame of reference. In some embodiments, the reference points may correspond to one or more teeth of the patient. In such cases, the reference points may be used to determine a transformation (i.e., a translation and/or a rotation) of the position or the orientation of the patient's teeth between the initial 3D oral model and the rough 3D oral model generated based on the one or more dental scans captured by the patient on a particular treatment milestone and date. In some embodiments, the rigid transformation may comprise a change in a position of a tooth (i.e., a translation in one or more directions) and/or a change in an orientation of a tooth (i.e., a rotation about one or more axes). The rigid transformation may be represented as six floating-point numbers corresponding to three or more degrees of freedom in translation and three or more degrees of freedom in rotation relative to three or more spatial axes in three dimensional space. In some embodiments, at least one of the initial 3D oral model and the updated 3D oral model may be saved as an STL file, a WRL file, a 3MF file, an OBJ, a FBX file, a 3DS file, an IGES file, or a STEP file.

In some embodiments, an image processing algorithm may be used to (i) generate a three-dimensional (3D) model of a dental structure of the subject based at least in part on the plurality of intraoral images, and (ii) determine a dental condition of the subject based at least in part on the three-dimensional model.

In some embodiments, the image processing algorithm may be configured to generate the 3D model based at least in part on an initial clinical scan of one or more intraoral regions of interest in the subject's mouth. In some embodiments, the initial clinical scan may comprise an initial three-dimensional (3D) model of the subject's dental structure that is generated before the plurality of intraoral images are captured using the camera of the mobile device.

In some embodiments, the three-dimensional (3D) model of the subject's dental structure may be generated based at least in part on motion data associated with a movement of the intraoral adapter relative to one or more intraoral regions of interest.

In some cases, the image processing algorithm may be configured to (i) generate a three-dimensional (3D) model of a dental structure of the subject based at least in part on the plurality of intraoral images. The three-dimensional model may be generated by overlaying and/or combining two or more intraoral images. In some cases, the three-dimensional model may be provided in an STL (Standard Triangle Language or Standard Tessellation Language) file format.

In some cases, the mobile device may comprise a stereoscopic camera. In such cases, the image processing algorithm may be configured to generate the three-dimensional oral model using one or more images or videos obtained using the stereoscopic camera. In some cases, the mobile device may comprise a depth sensor. In such cases, the image processing algorithm may be configured to generate the three-dimensional model using depth information (e.g., a depth map) obtained using the depth sensor.

In some cases, the image processing algorithm may be configured to generate the three-dimensional model using one or more aspects of passive triangulation. Passive triangulation may involve using stereo-vision methods to generate a three-dimensional model based on a plurality of images or videos obtained using a stereoscopic camera comprising two or more lenses. In other cases, the image processing algorithm may be configured to generate the three-dimensional model using one or more aspects of active triangulation. Active triangulation may involve using a light source (e.g., a laser source) to project a plurality of optical features (e.g., a laser stripe, one or more laser dots, a laser grid, or a laser pattern) onto one or more intraoral regions of a subject's mouth. Active triangulation may involve computing and/or generating a three-dimensional representation of the one or more intraoral regions of the subject's mouth based on a relative position or a relative orientation of each of the projected optical features in relation to one another. Active triangulation may involve computing and/or generating a three-dimensional representation of the one or more intraoral regions of the subject's mouth based on a relative position or a relative orientation of the projected optical features in relation to the light source or a camera of the mobile device.

In some cases, the image processing algorithm may be configured to generate the three-dimensional (3D) model based at least in part on an initial clinical scan of one or more intraoral regions of interest in the subject's mouth. The initial clinical scan may comprise an initial three-dimensional (3D) model of the subject's dental structure that is generated before the plurality of intraoral images are captured using the camera of the mobile device.

In some cases, the three-dimensional (3D) model of the subject's dental structure may be generated based at least in part on motion data associated with a movement of the intraoral adapter relative to one or more intraoral regions of interest. The motion data may be obtained using a motion sensor (e.g., an inertial measurement unit, an accelerometer, or a gyroscope).

The image processing algorithm may be configured to determine a dental condition of the subject based at least in part on the three-dimensional model. As described elsewhere herein, the dental condition may comprise (i) a movement of one or more teeth of the subject, (ii) an accumulation of plaque on the one or more teeth of the subject, (iii) a change in a color or a structure of the one or more teeth of the subject, (iv) a change in a color or a structure of a tissue adjacent to the one or more teeth of the subject, and/or (v) a presence or lack of presence of one or more cavities. In some cases, the three-dimensional model may be used to (i) predict a movement of one or more teeth of the subject, (ii) identify enamel wear patterns, (iii) create or modify a dental treatment plan, or (iv) generate or update an electronic medical record associated with a dental condition of the subject.

Providing Scans to Dentist

The computer-implement methods of the present disclosure may further comprise providing the one or more dental scans to the caregiver for an assessment of a dental condition based on the one or more dental scans. The one or more dental scans may be provided to and/or transmitted to the dentist through the chat user interface. The dentist may use the dental scans to update, modify, and/or change the patient-specific treatment timeline and/or the one or more treatment milestones and dates associated with the patient-specific treatment timeline. The dentist may use the dental scans to update, modify, and/or change the patient's dental treatment plan.

Caregiver Portal

The patient-side software application may be used in a compatible manner with a practitioner-side software application. For example, the practitioner-side software application may be configured to receive images, videos, or data sent by a patient using the patient-side software application. The practitioner-side software application may be configured to display the images, videos, or data sent by a patient using the patient-side software application to a dentist or a dental assistant for visual assessment or evaluation.

The practitioner-side software application may be configured to implement a computer-implemented method for remote dental monitoring. The method may comprise providing a caregiver portal for one or more caregivers to remotely monitor a dental condition of one or more patients.

The caregiver portal may comprise a graphical user interface that is configured to display one or more dental scans captured by the one or more patients. As described above, the one or more dental scans may comprise at least one of (i) one or more intraoral videos and (ii) a plurality of images derived from the one or more intraoral videos. In some cases, the caregiver portal may be configured to provide an interactive sidebar comprising a list of patients undergoing a dental treatment plan under the remote supervision of the caregiver. The interactive sidebar may be configured to display a chat user interface for each respective patient of the caregiver when the caregiver selects the patient's chat log or profile for viewing.

The chat user interface may be configured to facilitate remote communication between the caregiver and the patient. In some embodiments, the chat user interface may be configured to display the one or more dental scans captured by the one or more patients to enable viewing and access by the caregiver and the one or more patients while chatting. In some embodiments, the chat interface may be configured to display the one or more dental scans according to a patient-specific treatment timeline comprising one or more treatment milestones and dates.

When the caregiver selects a particular patient's chat log or profile for viewing, the chat user interface may be configured to display a patient-specific treatment timeline for the patient, as well as the treatment milestones and dates associated with the patient-specific treatment timeline and the one or more dental scans captured by the patient for each treatment milestone and date.

In some embodiments, the caregiver portal may comprise a task board interface configured to provide caregivers with information on one or more tasks associated with incoming patients, current patients, and preparation for dental treatment of the incoming patients or the current patients.

FIG. 1 illustrates an exemplary method for intraoral imaging. First, a subject may reach a milestone and date associated with a dental treatment (10). Next, the intraoral imaging system may provide the subject with a notification to take an intraoral scan (11). Next, the subject may connect a mobile device to an intraoral adapter (12). Next, the subject may use the mobile device to initiate an intraoral scan (13). The intraoral scan may be initiated and performed using the software applications provided and described herein. The software application may provide one or more instructions for the subject to stand in front of a mirror and to adjust a position and/or an orientation of the mobile device to take one or more intraoral scans (14). Next, the software application may provide guided instructions for the subject to take one or more intraoral scans (15). Next, the subject may take a plurality of intraoral scans (16). The plurality of intraoral scans (e.g., images or videos) may comprise a left to right or a right to left movement of the intraoral adapter while the subject has a closed bite. The plurality of intraoral scans may comprise a left to right or a right to left movement of the intraoral adapter while the subject has an open bite. The plurality of intraoral scans may comprise one or more scans of an upper dental arch and/or a lower dental arch of the subject. Next, the software application installed on the mobile device may assess whether or not the intraoral scans are acceptable (17). The acceptability of the intraoral scans may be assessed based on lens cleanliness, image clarity, sufficient focus, centering of the intraoral images, and/or whether the subject has achieved a full occlusion capture including internal edges of a left dental arch, a right dental arch, a top dental arch, and/or a bottom dental arch. If an intraoral scan is not acceptable, the subject may be prompted to perform another intraoral scan. If the intraoral scan is acceptable, the mobile device may upload the intraoral scan to a patient's electronic dental record (18). Next, the intraoral scans may be processed to determine a dental condition of the subject (19). The dental condition may comprise (i) a movement of one or more teeth of the subject, (ii) an accumulation of plaque on the one or more teeth of the subject, (iii) a change in a color or a structure of the one or more teeth of the subject, (iv) a change in a color or a structure of a tissue adjacent to the one or more teeth of the subject, and/or (v) a presence or lack of presence of one or more cavities. In some cases, the image processing unit may use the plurality of intraoral images to (i) predict a movement of one or more teeth of the subject, (ii) identify enamel wear patterns, (iii) create or modify a dental treatment plan, and/or (iv) generate or update an electronic medical record associated with a dental condition of the subject.

The software applications disclosed herein may be used with any type of device or intraoral adapter that is configured to permit capture of a patient's teeth or dental structure. The intraoral adapter may be configured to permit the patient to capture one or more intraoral images or videos using a mobile device or a smartphone. The intraoral adapter may be configured to position the mobile device or smartphone such that the patient is able to capture the images or videos from one or more predetermined positions or viewing angles.

Figure 2A:
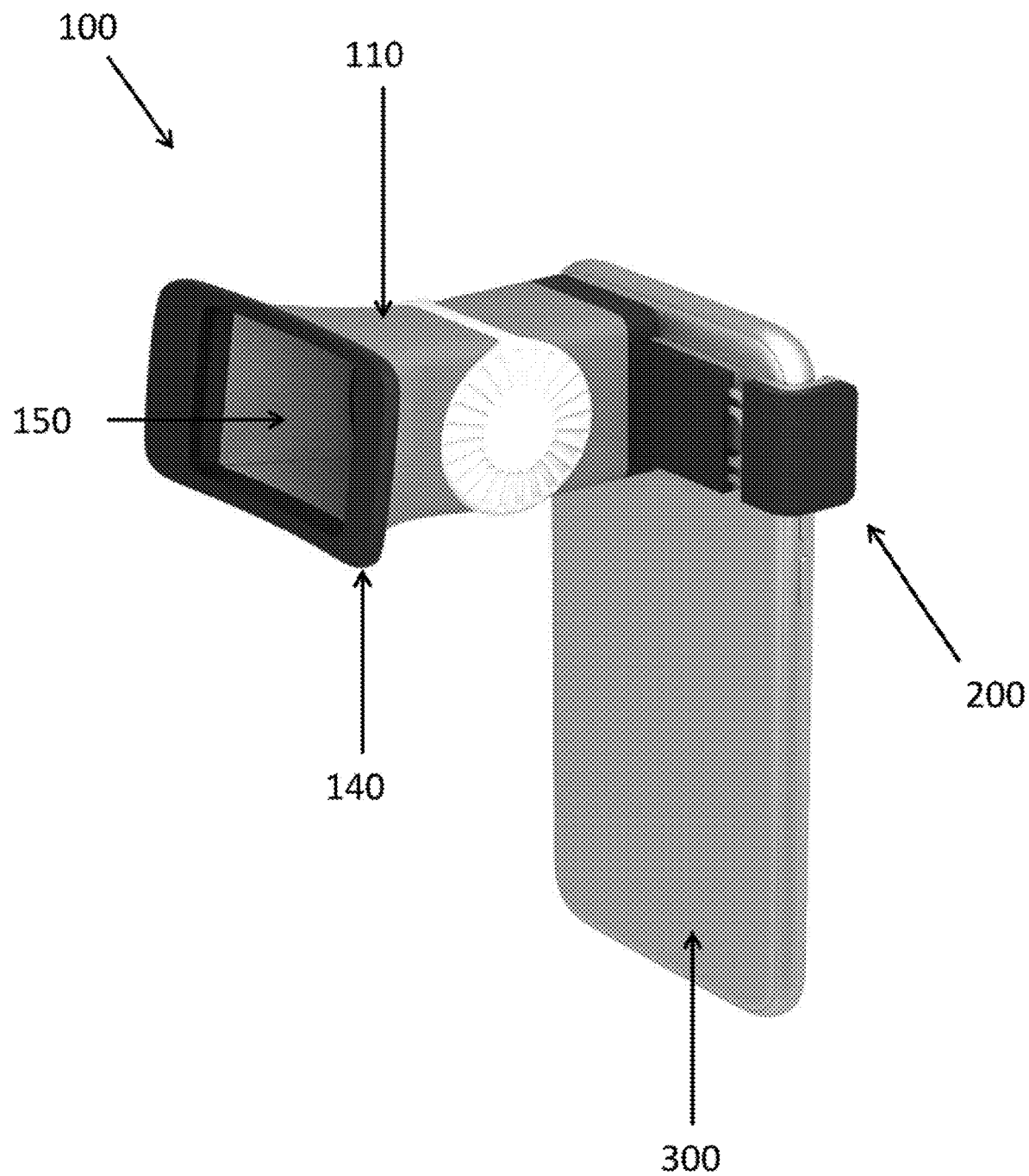
FIGS. 2A, 2B, 2C, 2D, and 2E schematically illustrate an exemplary intraoral adapter to which a mobile device can be coupled for intraoral scanning, in accordance with some embodiments.
Figure 2B:
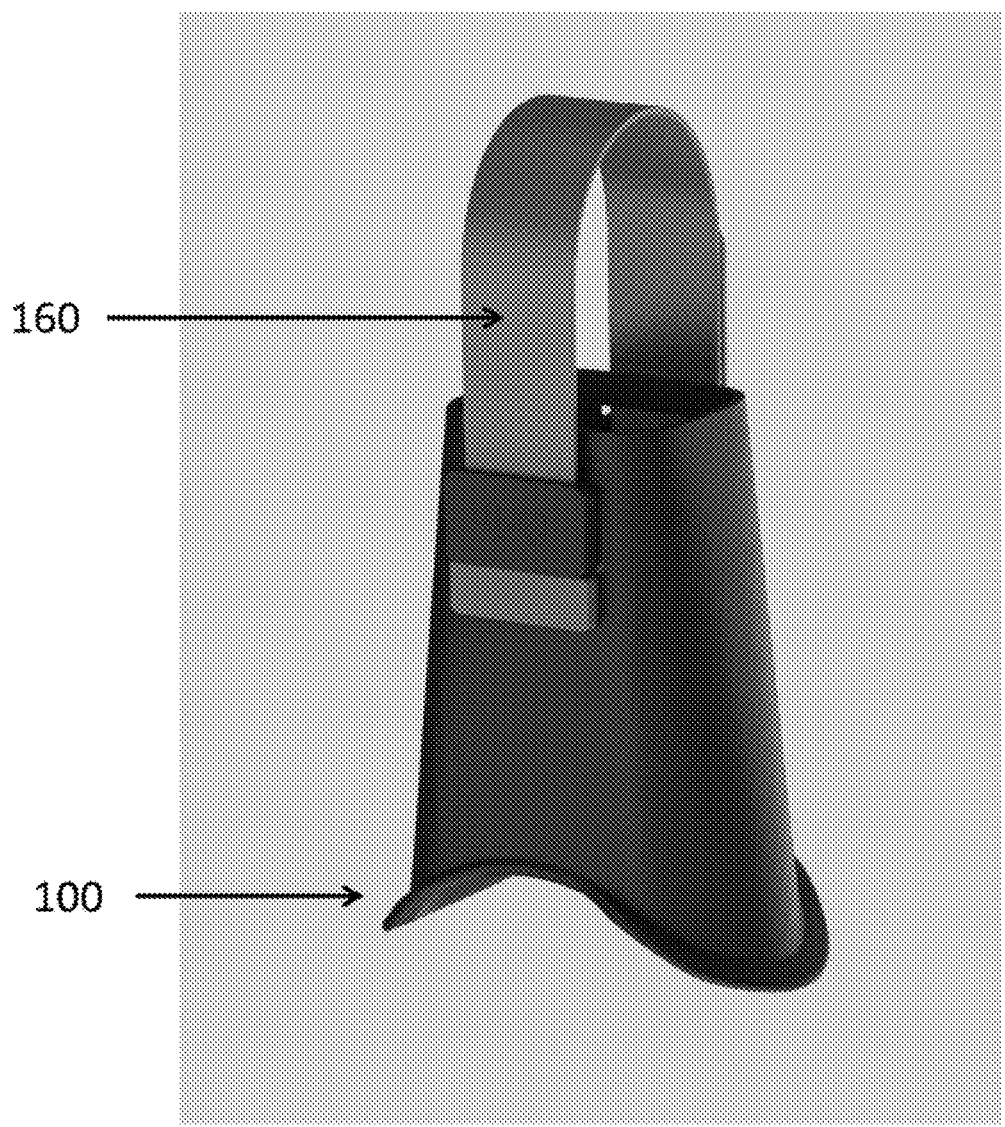
Figure 2C:
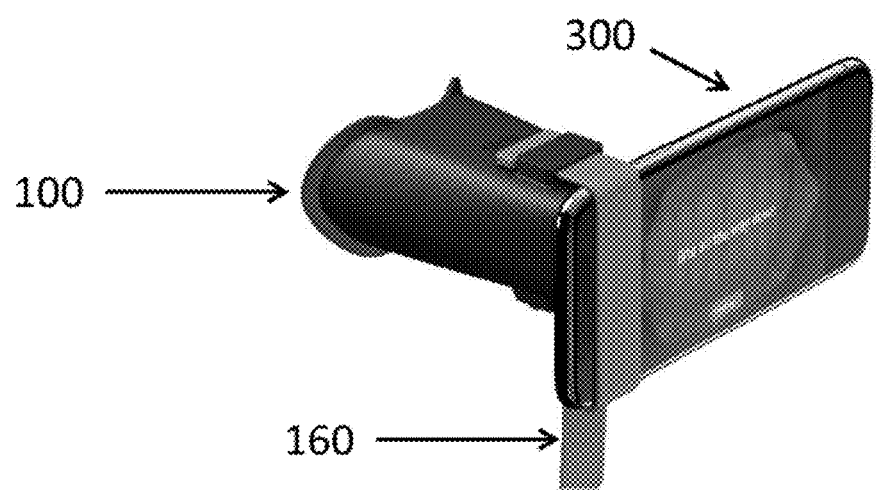
Figure 2D:
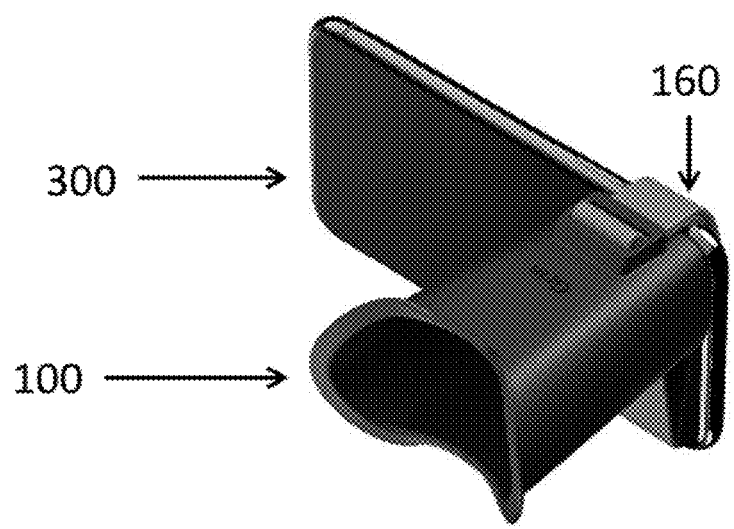
Figure 2E:
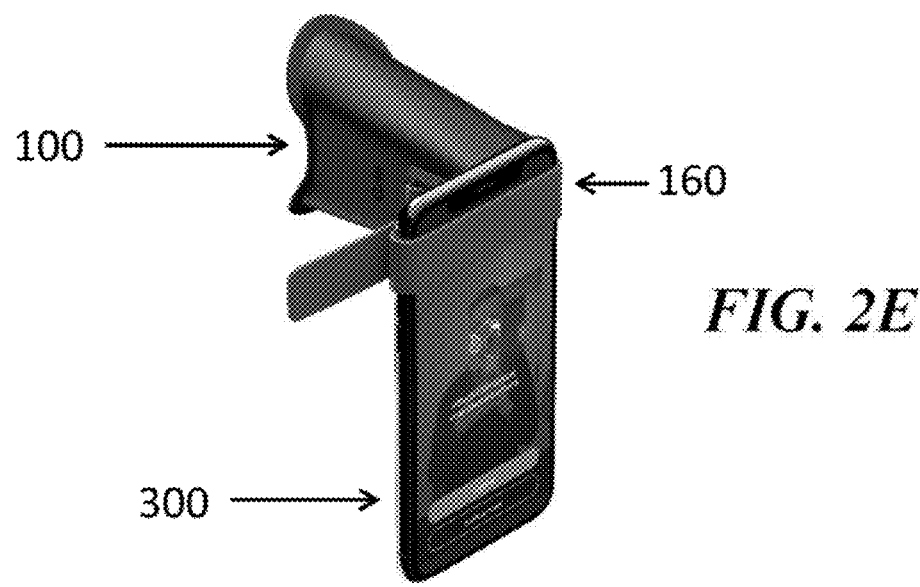

FIG. 2A illustrates an example of an intraoral adapter 100 that may be used with the systems and methods disclosed herein. The intraoral adapter 100 may comprise an elongated housing 110 with a mounting mechanism 200 and a mobile device 300 coupled to the intraoral adapter 100 via the mounting mechanism 200. The mounting mechanism 200 may be configured to couple the mobile device 300 to the intraoral adapter 100 such that a longitudinal axis of a viewing channel 150 of the intraoral adapter 100 is substantially aligned with an optical axis of one or more cameras of the mobile device 300. The mounting mechanism 200 may be configured to mechanically engage with the mobile device 300 or a casing of the mobile device 300. In some embodiments, the mounting mechanism may comprise an elastic band, a clamp, a hook, a magnet, a bracket, or a holder.

The optical axis of the one or more cameras of the mobile device 300 may be aligned with one or more intraoral regions of the subject's mouth when a flange 140 of the elongated housing 110 is positioned between a tooth portion and a gum portion of the subject's mouth. The mobile device may comprise an imaging device (e.g., a camera) that can be used to capture the one or more intraoral images or videos.

The viewing channel 150 of the elongated housing 110 may be configured to define a field of view of an intraoral region of a subject's mouth. The field of view may be sized and/or shaped to permit one or more cameras of the mobile device 300 to capture one or more images or videos of one or more intraoral regions in a subject's mouth. In some cases, the one or more images or videos may comprise one or more intraoral images or videos showing a portion of a subject's mouth. In some cases, the one or more images or videos may comprise one or more intraoral images showing a full dental arch of the subject.

The flange 140 may be sized and shaped to couple the intraoral adapter to the subject's mouth when the flange 140 is positioned between a gum portion and a tooth portion of the subject's mouth. The intraoral adapter 100 may be suspended from the subject's mouth when the flange 140 is positioned between the gum portion and the tooth portion of the subject's mouth. The gum portion and the tooth portion may be in contact with a first side of the flange 140 and a second side of the flange 140 to support a weight of the intraoral adapter 100 when the intraoral adapter 100 is suspended from the subject's mouth. The flange 140 may be sized and shaped to permit the subject to move the intraoral adapter and/or to adjust a position or an orientation of the intraoral adapter relative to one or more intraoral regions in the subject's mouth. Adjusting the position or the orientation of the intraoral adapter relative to one or more intraoral regions in the subject's mouth may also adjust a position or an orientation of the camera of the mobile device relative to the one or more intraoral regions in the subject's mouth. Adjusting a position or an orientation of the camera of the mobile device relative to the one or more intraoral regions in the subject's mouth may further adjust a relative position and/or a relative orientation of an optical axis of the camera relative to the one or more intraoral regions in the subject's mouth. The flange 140 may remain between the gum portion and the tooth portion of the subject's mouth while the subject moves the intraoral adapter around in the subject's mouth. The flange 140 may be sized and shaped to permit the subject to capture one or more intraoral images or videos of a full dental arch of the subject. In any of the embodiments described herein, the flange 140 of the intraoral adapter may be positioned outside the field of view defined by the viewing channel of the intraoral adapter.

FIGS. 2B, 2C, 2D, and 2E illustrate another embodiment of an intraoral adapter 100 that may be used to capture intraoral images or videos. In some cases, the intraoral adapter 100 may comprise an attachment mechanism 160 for coupling a mobile device 300 to the intraoral adapter 100. The attachment mechanism 160 may comprise, for example, a strap for securing the mobile device 300 to the intraoral adapter 100. The strap may comprise a flexible and/or compliant material, such as silicone. In some cases, the strap may comprise any biocompatible material, or any material that is dishwasher safe. The strap may be adjustable to enable a user to couple various mobile devices having different sizes, shapes, and/or form factors. The adjustability of the strap may provide several advantages, including improved compatibility with different mobile devices having distinct camera configurations, or imaging sensors disposed on different portions or locations on the mobile device.

The software application may permit the patient to take one or more intraoral images or videos. The intraoral images or videos may be capture while the patient is moving the intraoral adapter, or after the patient moves the intraoral adapter to a predetermined location.

FIG. 3 illustrates a plurality of intraoral images that may be captured using the software application. The plurality of intraoral images may comprise a front view, a side view, a bottom view, and/or a top view of one or more portions of the subject's upper dental arch or lower dental arch. The one or more intraoral images may be captured while the subject is biting down (i.e., when the subject's upper dental arch and lower dental arch are in contact with or adjacent to each other). The plurality of intraoral images may be captured while the subject is not biting down completely (i.e., when at least a portion of the subject's upper dental arch and lower dental arch are not in contact with each other, or when the subject's upper dental arch and lower dental arch are separated by a separation distance). The plurality of intraoral images may comprise images of different intraoral regions within the subject's mouth.

Patient GUI

Figure 5A:
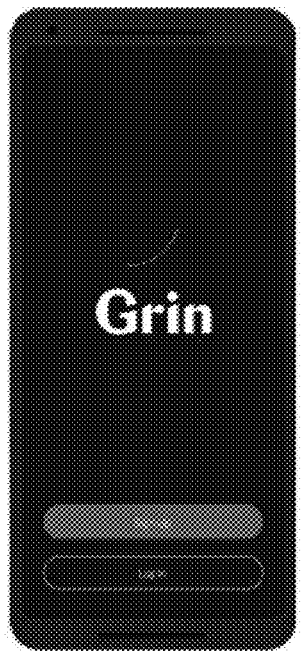
FIGS. 5A, 5B, 5C, and 5D schematically illustrate various user interfaces for patients to sign up for remote dental monitoring, in accordance with some embodiments.
Figure 5B:
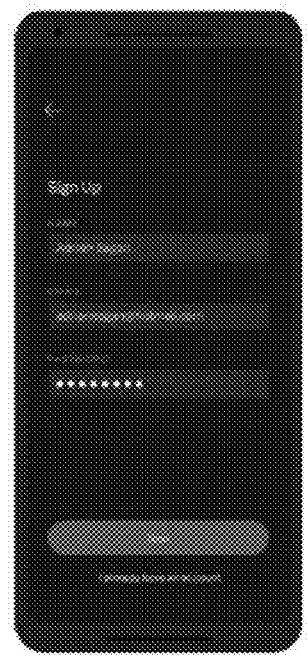
Figure 5C:
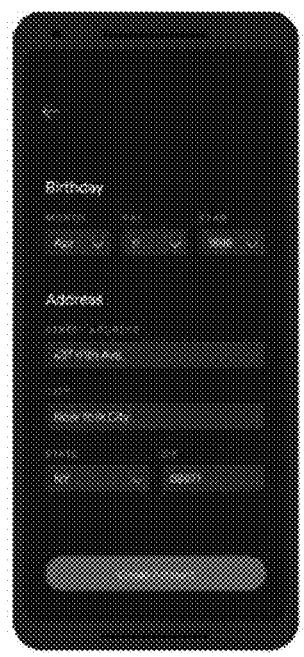
Figure 5D:
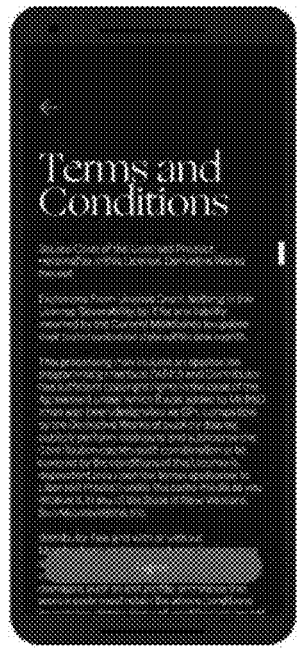

Provided herein are various exemplary embodiments of a mobile generated user interface (GUI) for a patient-side remote dental monitoring application. FIG. 5A shows an exemplary mobile generated user interface (GUI) for a home page that allows a patient to log in to or sign up for the dental monitoring application. To sign up for the dental monitoring application, the user may enter their name, email address, and select a password, per FIG. 5B. In some embodiments, per FIG. 5C the new patient is then prompted to enter their birthday (e.g. month, day, year) and address (e.g. street address, city, state, zip code). In some embodiments, per FIG. 5D the new patient is further prompted to accept the terms and conditions of the mobile service.

Figure 6A:
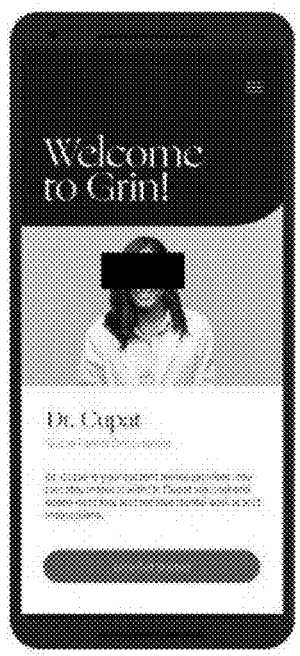
FIGS. 6A, 6B, 6C, and 6D schematically illustrate various user interfaces for patients to view their account information and dentist information, in accordance with some embodiments.
Figure 6B:

Per FIG. 6A, after the patient is registered and logged in, the new patient, in some embodiments, is shown a description of their caregiver. During registration, the patient's account may be associated with the patient's caregiver. The patient may press a button to get started with using the software application, in which case the patient may be presented with a main menu that provides an overview of the dental monitoring application. FIG. 6B shows an exemplary patient GUI for a menu page that allows the patient to access a chat feature, account information, a tutorial, and a feature to refer a friend.

Figure 6C:
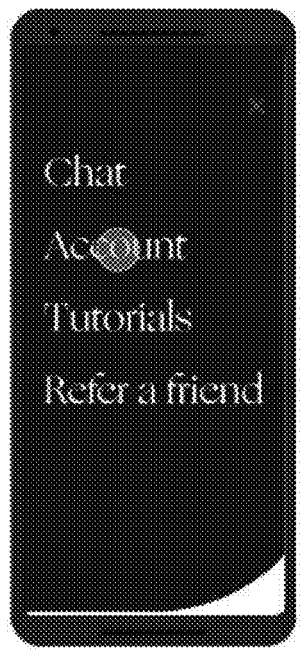
Figure 6D:
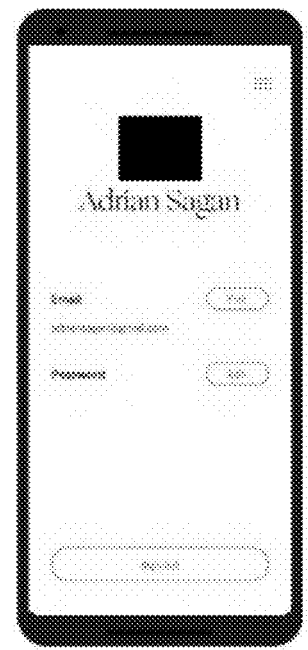

As shown in FIG. 6C and FIG. 6D, the software application may permit the patient to access his or her account by pressing an account button. The patient may access his or her account to edit email and/or password information. The patient may access his or her account to edit any other personal information provided when creating and/or registering the account.

Figure 7A:
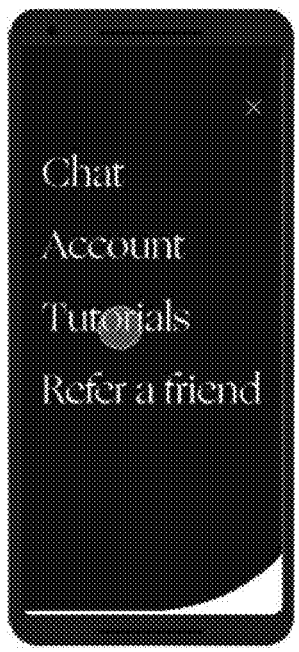
FIGS. 7A, 7B, 7C, and 7D schematically illustrate various user interfaces for patients to view tutorials and refer friends, in accordance with some embodiments.
Figure 7B:
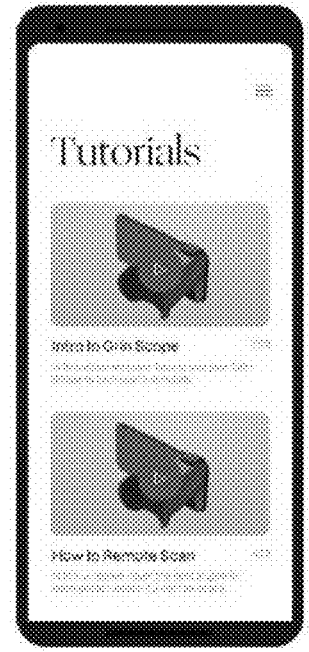

As shown in FIG. 7A and FIG. 7B, the software application may permit the patient to access one or more tutorials by pressing a tutorials button. The one or more tutorials may provide the patient with an introduction to one or more intraoral adapters that are compatible with the software application, and how to use the one or more compatible intraoral adapters to take intraoral scans remotely. In some cases, the one or more tutorials may provide the patient with an instructional video on how to perform the remote intraoral scans, and a graphical illustration of the best angles for each photo needed to perform the remote scan. The one or more tutorials may also provide the patient with an instructional video or live guidance on how to optimally position or move the compatible intraoral adapter or the mobile device coupled to the compatible intraoral adapter relative to patient's teeth to capture the intraoral images or videos.

Figure 7C:
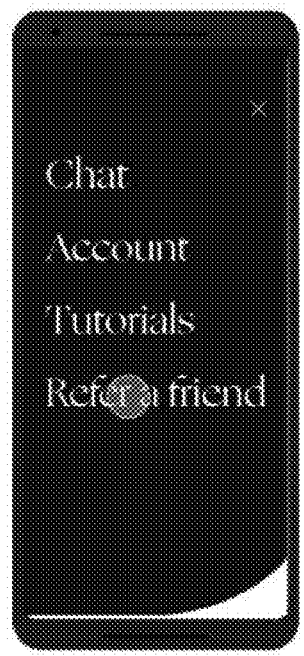
Figure 7D:
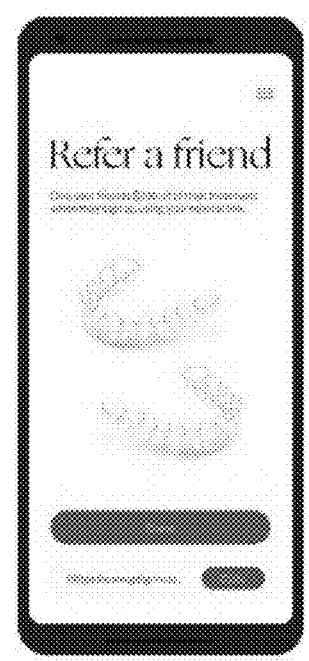

As shown in FIG. 7C and FIG. 7D, the software application may permit the patient to refer a friend by pressing a refer a friend button. The patient may then share a link to another third party who may be interested in or may be required to undergo remote dental monitoring. The link may be copied for sharing via email or another messaging application. The link may be used by the third party to download the remote monitoring application and to begin remote dental monitoring.

The patient may press the chat button or icon to initiate a private chat with the patient's dentist or a dental assistant of the patient's dentist. As shown in FIGS. 8A, 8B, 8C, and 8D, in some cases, the software application may provide a chat environment for the patient to chat with the dentist. The user interface shown in FIGS. 8A, 8B, 8C, and 8D is an exemplary patient GUI that enables the patent to chat with their care provider and/or an account assistant. In some cases, the chat environment may provide a camera icon for the patient to take one or more dental scans. The one or more dental scans may comprise a video or a plurality of images of various intraoral regions of the patient. The one or more dental scans may be uploaded to the chat environment for the dentist to view, analyze, and/or annotate.

In some cases, pressing the chat icon may initiate a messaging interface between the patient and a dentist. Alternatively, pressing the chat icon may initiate a messaging interface between the patient and an automated, dynamic chat assistant. The dynamic chat assistant may be configured to ask the patient one or more questions about how a treatment is going to (i) assess a patient's need to undergo a dental treatment plan, (ii) assess the patient's compliance with a dental treatment plan, or (iii) assess a need for the patient to modify a current dental treatment plan or undergo a new dental treatment plan. The one or more questions presented to the patient may be customized or tailored based on a treatment history of the patient, previous scans taken by the patient, or a dentist's notes or commentary in response to the previous scans. In some cases, the dynamic chat assistant may be configured to walk the patient through one or more steps to obtain new dental scans. In other cases, the dynamic chat assistant may be configured to review previous dental scans with the patient.

Figure 8A:
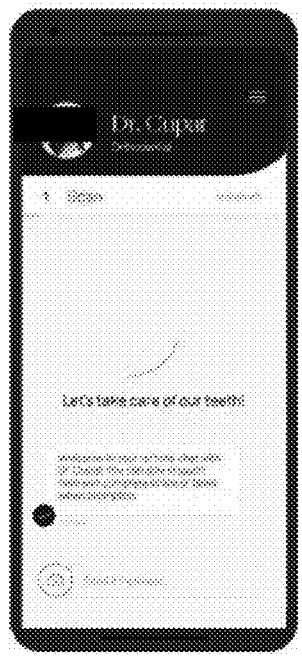
FIGS. 8A, 8B, 8C, and 8D schematically illustrate a chat user interface for a patient-side remote dental monitoring software application, in accordance with some embodiments.
Figure 8B:
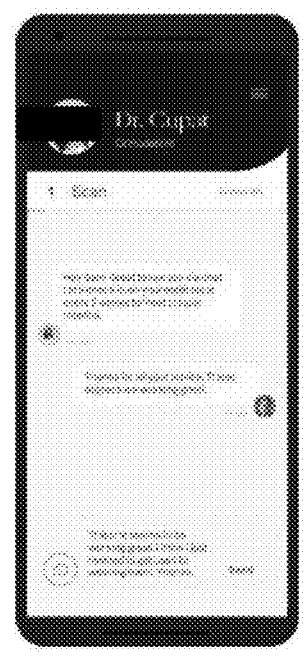
Figure 8C:
Figure 8D:
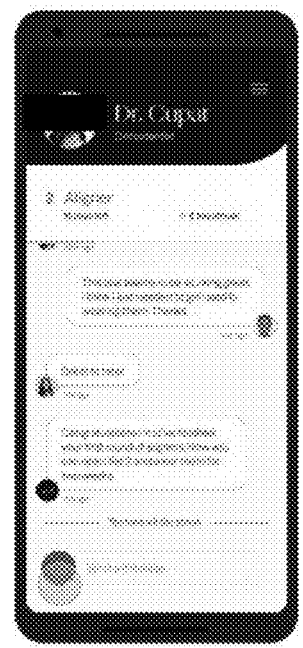
Figure 9A:
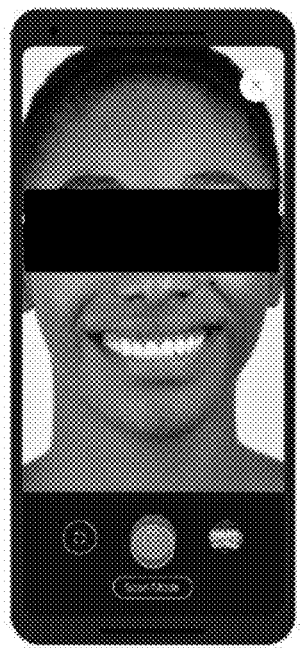
FIGS. 9A and 9B schematically illustrate a user interface for patients to capture and share dental scans and/or selfie images, in accordance with some embodiments.
Figure 9B:

In some embodiments, the dental monitoring application allows the patient to send an image to their dentist or caregiver. FIG. 8D shows an exemplary patient graphical user interface (GUI) for sending a photo via the chat feature. When the patient presses the camera icon, the user interface may be configured to open the image and video capture GUI illustrated in FIG. 9A to begin capturing, or recapturing one or more images or videos of the patient. In some cases, the one or more images or videos may be of the patient while the patient is wearing an aligner. In some cases, the one or more images or videos may be of the patient when the patient is not wearing an aligner. In some cases, the one or more images or videos may be one or more intraoral scans. The image and video capture GUI may permit the patient to switch between one or more cameras (e.g., one or more front-facing cameras and/or one or more rear-facing cameras) of the mobile device for image or video capture. In some cases, the image and video capture GUI may permit the patient to switch between different scan modes. The different scan modes may allow the patient to take different types of images or videos (e.g., a picture or a video of the patient's face when the patient is smiling, or one or more intraoral images or videos of a dental structure of the patient). In some cases, the image and video capture GUI may permit the patient to save captured images or videos to a gallery of the patient's mobile device. In some cases, the image and video capture GUI may permit the patient to view prior images or videos taken by the patient. After the patient captures one or more images or videos, the patient may review the captured images or videos before sharing them with the dentist. After the patient captures one or more images or videos, the images or videos may be sent via the chat interface to the dentist or caregivers, as illustrated in FIG. 9B.

Figure 9C:
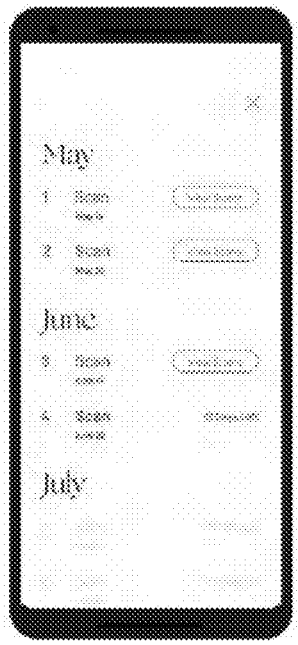
FIG. 9C schematically illustrates a treatment timeline with milestone dates, in accordance with some embodiments.

In some embodiments, the chat interface may comprise an interactive button that may be pressed by the patient to access a treatment timeline associated with the patient's dental treatment, as shown in FIG. 9C. The treatment timeline may comprise a visual representation or roadmap of the patient's treatment. The visual representation may provide a schedule for the treatment. The schedule may comprise one or more milestones corresponding to different steps of the treatment plan to be completed by the patient by certain milestone and dates. The schedule may comprise one or more milestones or milestone dates by which or after which a patient is encouraged or instructed to capture one or more images, videos, or dental scans. The treatment timeline may provide a list of milestone and dates and a chronological ordering of the various scans captured by the patient during the treatment process. The treatment timeline may provide a plurality of buttons which may be pressed by the patient to access previous scans. The treatment timeline may show the patient how many days are left until a next scan is required or suggested. The patient may be able to use the timeline to determine how many milestones have been completed, and how many scans remain before completion of the treatment.

Figure 9D:
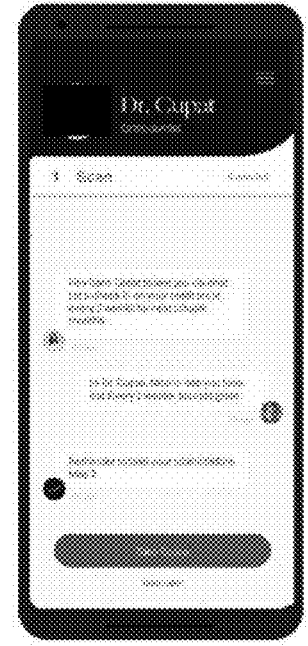
FIG. 9D schematically illustrates a chat user interface that is configured to enable patients to capture dental scans, in accordance with some embodiments.
Figure 10A:
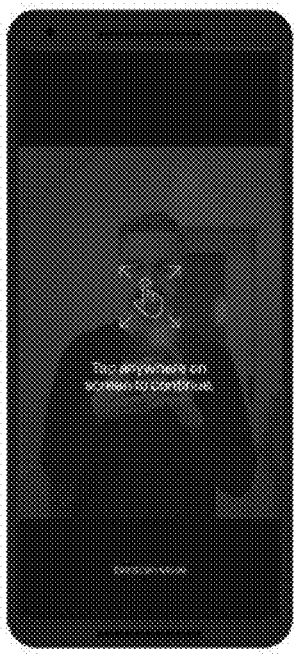
FIGS. 10A, 10B, 10C, and 10D schematically illustrate visual and/or textual guidance to aid patients in capturing dental scans, in accordance with some embodiments.
Figure 10B:
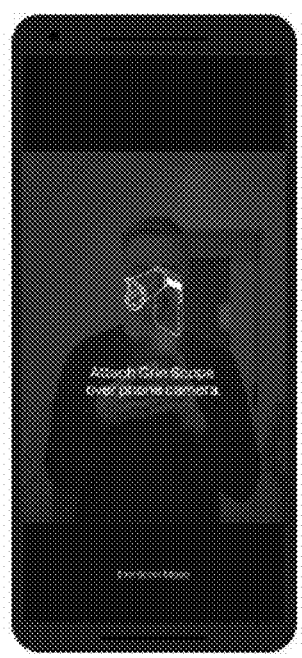
Figure 10C:
Figure 10D:
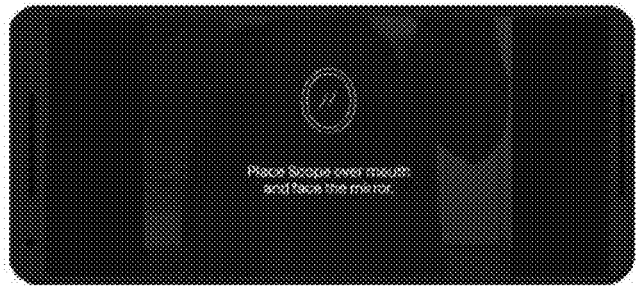

In some embodiments, when a milestone and date arrives, the chat interface and/or the dentist may prompt the patient to perform a milestone scan, as illustrated in FIG. 9D. When prompted to take one or more scans, the patient may press a first button to take the scans, or may press a second button to take the scans at a later time. If the patient presses the first button, the remote monitoring application may be configured to enter a scan mode. Per FIGS. 10A-10D, the milestone scan mode GUI may prompt or instruct the patient to tap anywhere on the screen to initiate scanning. The milestone scan mode GUI may prompt or instruct the patient to attach a compatible intraoral adapter to the patient's mobile device such that a camera of the mobile device is optically aligned with a viewing channel of the intraoral adapter. The milestone scan mode GUI may prompt or instruct the patient to insert a portion of the intraoral adapter (e.g., a flange of the intraoral adapter) inside the patient's mouth to permit imaging of one or more intraoral regions in the patient's mouth. The milestone scan mode GUI may prompt or instruct the patient to face a mirror so that the patient may view and follow the instructions provided by the milestone scan mode GUI while moving the intraoral adapter to capture one or more images or videos of the patient's teeth. In cases where the patient uses a rear-facing camera of the mobile device to capture the one or more images or videos, the patient may use a reflection of himself or herself in the mirror to view the instructions provided on a screen of the mobile device, since the screen may be oriented towards the mirror.

Figure 11A:
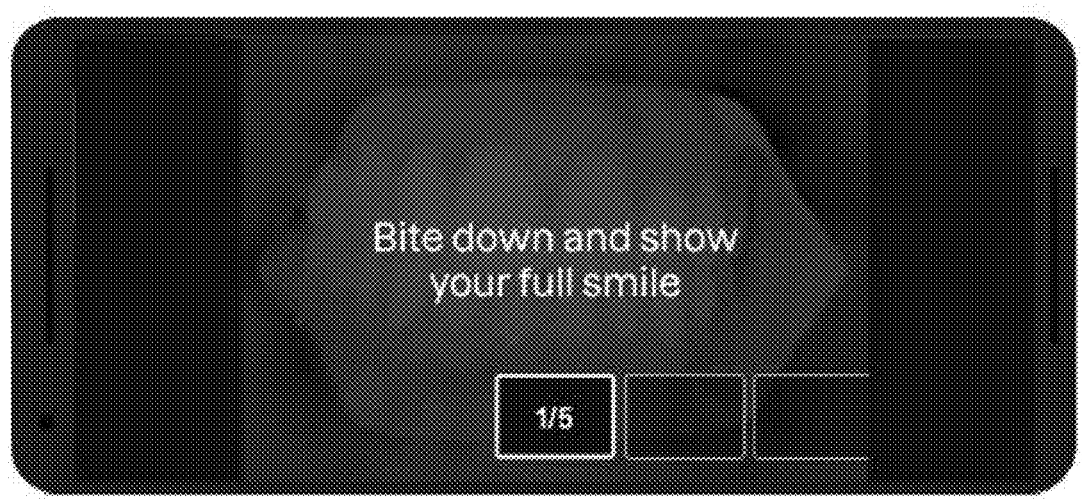
FIGS. 11A, 11B, 12A, 12B, 13A, 13B, 14A, 14B, 15A, 15B, and 16A schematically illustrate a plurality of user interfaces for capturing dental scans using a patient-side remote dental monitoring software application, in accordance with some embodiments.
Figure 11B:
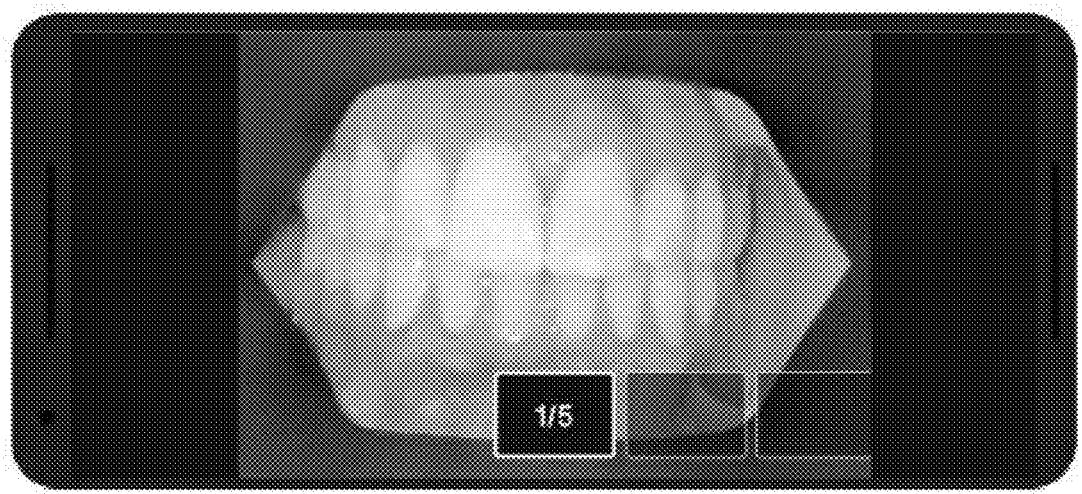
Figure 12A:
Figure 12B:
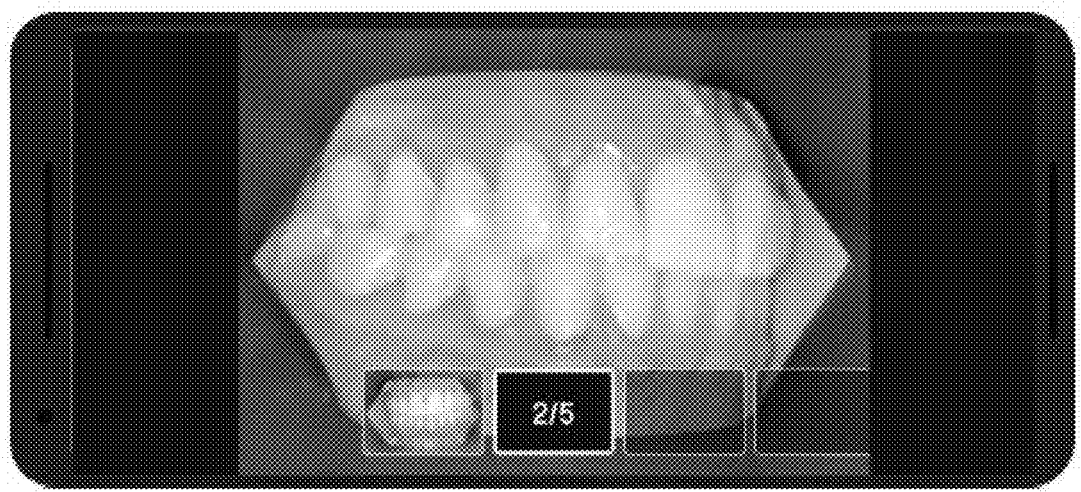
Figure 13A:
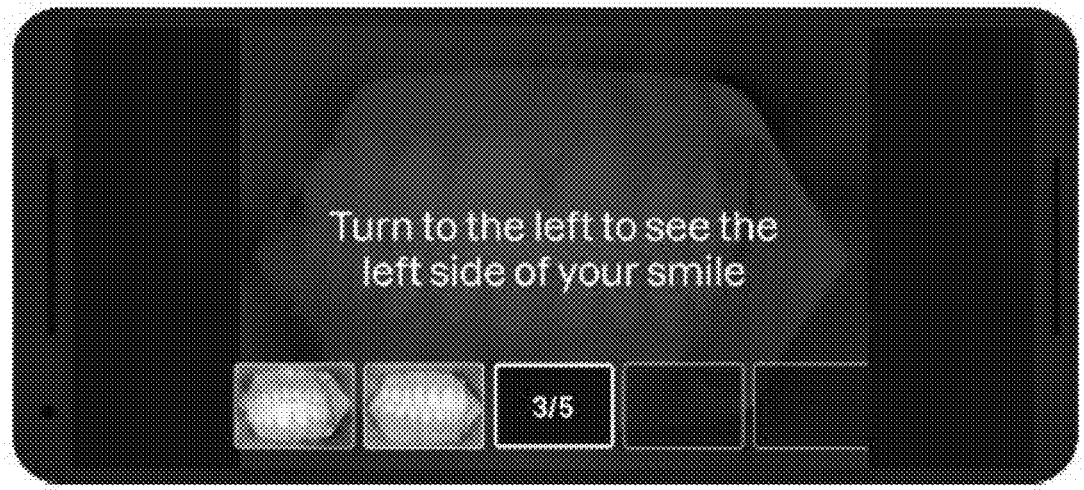
Figure 13B:
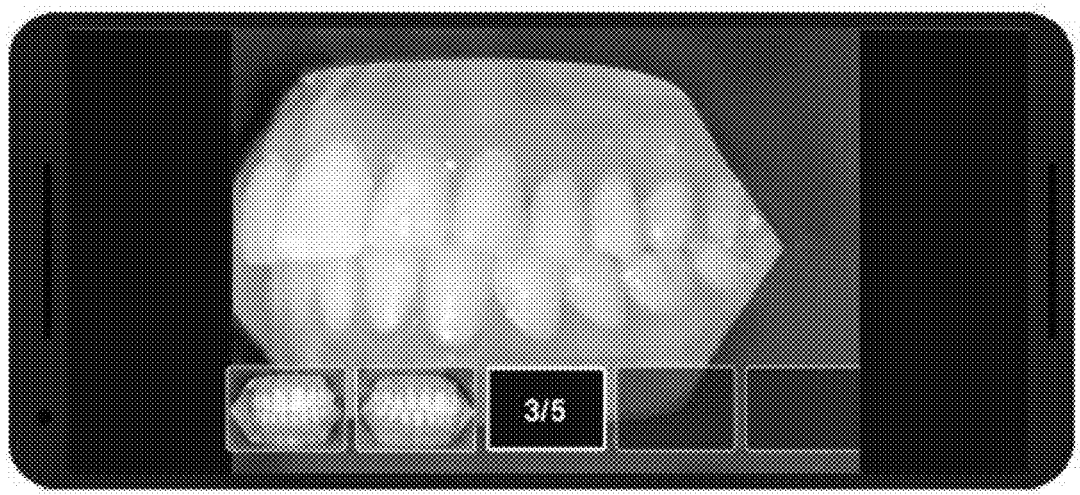
Figure 14A:
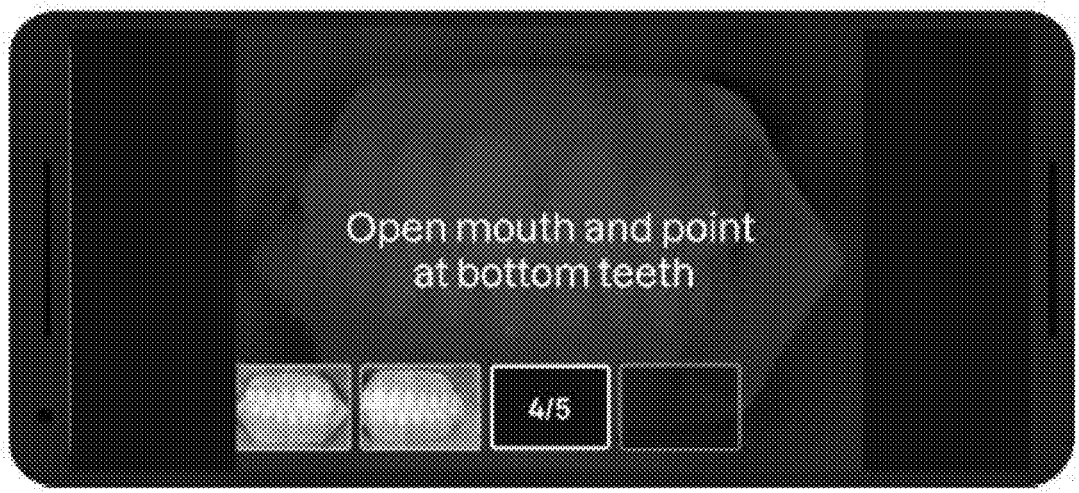
Figure 14B:
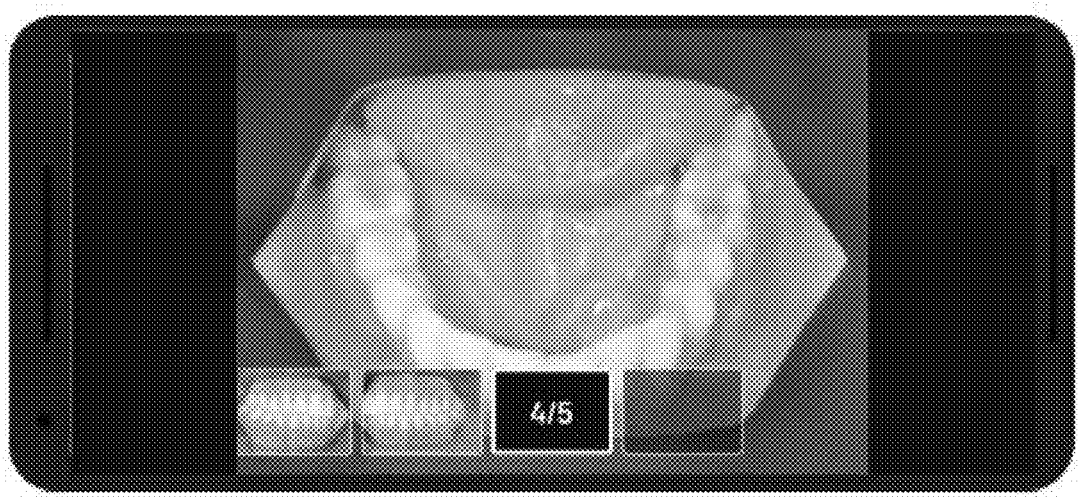
Figure 15A:
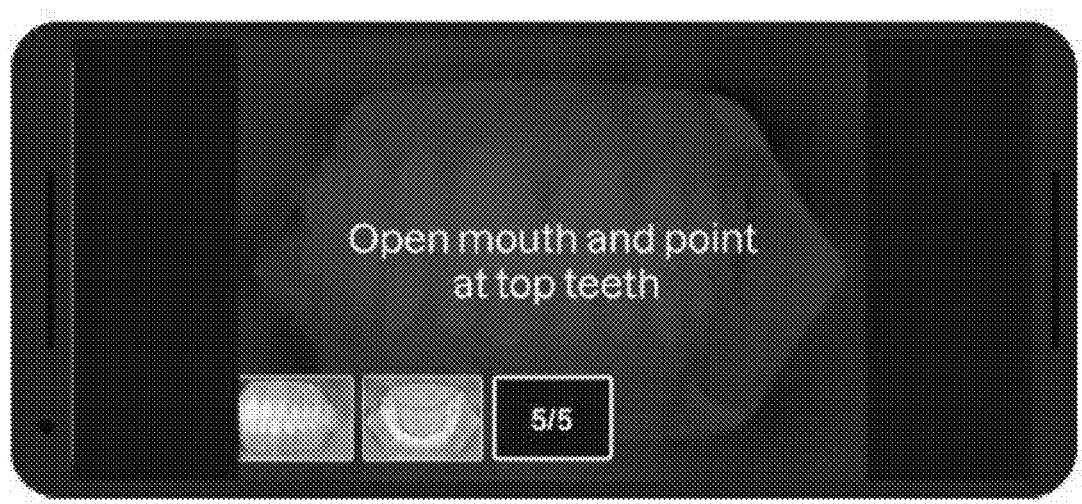
Figure 15B:
Figure 16A:
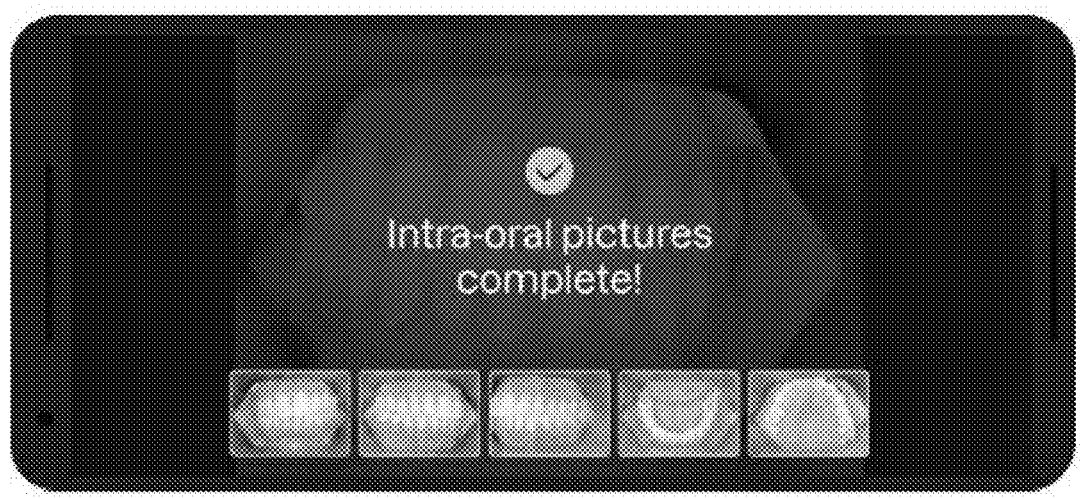

In some embodiments, per FIGS. 11A-11B, the milestone scan mode GUI may be configured to instruct the patient to bite down and show a full smile to capture a first milestone scan. The first milestone scan may comprise one or more intraoral images taken from different angles, as shown in FIG. 3. Alternatively, the first milestone scan may comprise one or more videos of an intraoral region of the patient's mouth. The one or more videos may be spliced into a plurality of still images later for review by the dentist. The milestone scan mode GUI may provide a plurality of boxes near a bottom portion of the GUI to show how many required scans have been taken or how many required scans are remaining. The plurality of boxes may provide a visual representation of the scans taken for each required angle. In some embodiments, per FIGS. 12A-12B, the exemplary milestone scan mode GUI may then instruct the patient to turn to the right to capture a second milestone scan of a right side of the patient's smile. In some embodiments, per FIGS. 13A-13B, the exemplary milestone scan mode GUI may then instruct the patient to turn to the left to capture a third milestone scan of a left side of the patient's smile. In some embodiments, per FIGS. 14A-14B, the exemplary milestone scan mode GUI may then instruct the patient to point the camera to their bottom teeth to capture a fourth milestone scan of a bottom dental arch of the patient. In some embodiments, per FIGS. 15A-15B, the exemplary milestone scan mode GUI may then instruct the patient to point the camera to their top teeth to capture a fourth milestone scan of a top dental arch of the patient. Thereafter, in some embodiments, per FIG. 16A, the exemplary milestone scan mode GUI may display an indication of a completed milestone scan. The exemplary milestone scan mode GUI may be further configured to display a series of intraoral images taken by the patient in accordance with the instructions provided by the exemplary milestone scan mode GUI.

In some alternative embodiments, the exemplary milestone scan mode GUI may be configured to instruct the patient to capture one or more intraoral videos. In such cases, the exemplary milestone scan mode GUI may provide the patient with instructions on how to move the mobile device or the intraoral adapter coupled to the mobile device to capture a plurality of different views of the patient's teeth. The plurality of different views may comprise a front view of the patient's full smile, a left view of the patient's smile, a right view of the patient's smile, a view of the patient's bottom dental arch, and/or a view of the patient's top dental arch.

In some cases, the one or more intraoral videos captured by the patient may be provided to the dentist or caregiver. The dentist may view the one or more intraoral videos and may obtain one or more still images from the intraoral videos. The one or more still images may correspond to different views of various intraoral regions of the patient's mouth, such as, for example, a front view of the patient's full smile, a left view of the patient's smile, a right view of the patient's smile, a view of the patient's bottom dental arch, and/or a view of the patient's top dental arch. Capturing one or more videos may provide a benefit over capturing intraoral images because the videos may permit the dentist to derive optimal still images of the patient's teeth without relying solely on the patient's ability to capture acceptable images for analysis.

Figure 16B:
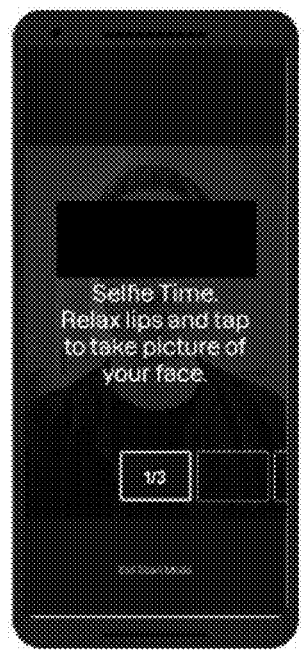
FIGS. 16B, 17A, 17B, 17C, 17D, 18A, and 18B schematically illustrate a plurality of user interfaces for capturing selfie scans using a patient-side remote dental monitoring software application, in accordance with some embodiments.
Figure 17A:
Figure 17B:
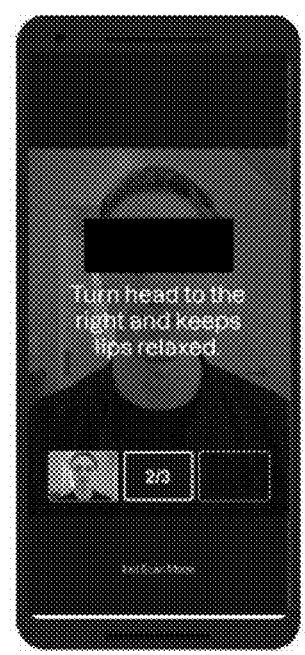
Figure 17C:
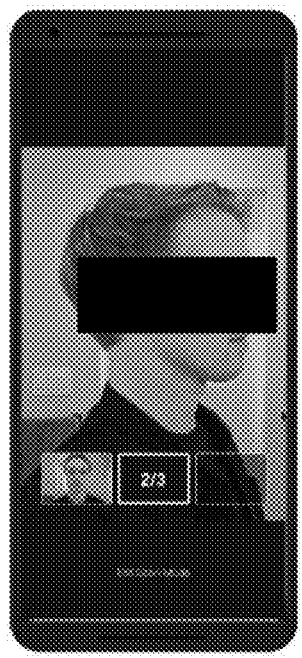
Figure 17D:
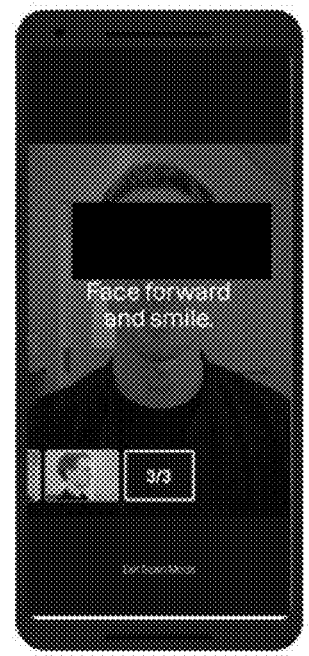

As shown in FIG. 16B, in some cases the milestone scan mode GUI may be further configured to provide the patient with on-screen instructions for the patient to capture a plurality of selfies. The plurality of selfies may comprise one or more selfie images or selfie videos of the patient. The plurality of selfies may be captured before or after the patient captures the one or more intraoral images or videos using the milestone scan mode GUI. The plurality of selfies may be required to complete the milestone scans. In some embodiments, the GUI may be configured to instruct the patient to relax his or her lips during the capture of the selfie milestone scans. As shown in FIG. 17A, in some embodiments, a first selfie milestone scan may be captured of a front view of the patient. As shown in FIG. 17B, in some embodiments, the GUI may instruct the patient to turn his or her head in a left and/or right direction and to keep his or her lips relaxed in preparation for a second selfie milestone scan. The second selfie milestone scan may then be captured for a left side and/or a right side of the patient's face as shown in FIG. 17C. As shown in FIG. 17D, once the second selfie milestone scan is completed, the GUI may instruct the patient to face forward and smile in preparation for a third selfie milestone scan. As shown in FIGS. 17A-17D, the selfie scan GUI may provide a plurality of boxes near a bottom portion of the selfie scan GUI to show how many required selfie scans have been taken and/or how many required scans are remaining. The plurality of boxes may provide a visual representation of the selfie scans taken for each required angle.

Figure 18A:
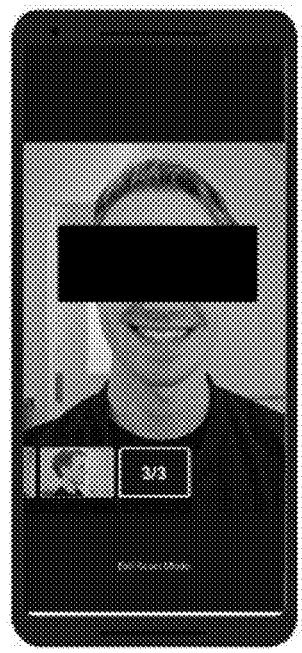
Figure 18B:
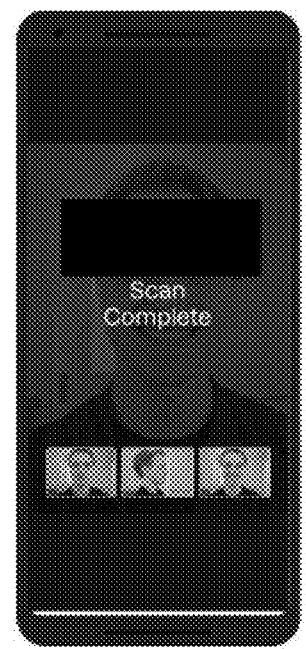
Figure 18C:
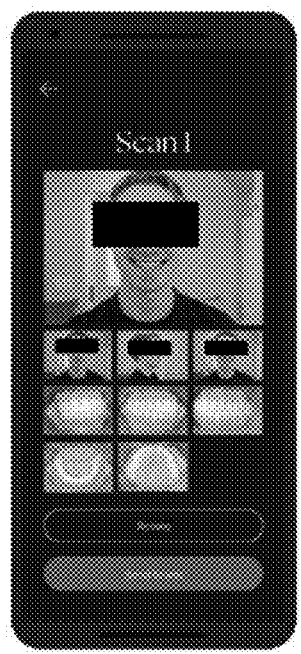
FIG. 18C schematically illustrates a plurality of dental scans and/or selfie scans that may be sent to a dentist using a patient-side remote dental monitoring software application, in accordance with some embodiments.
Figure 18D:
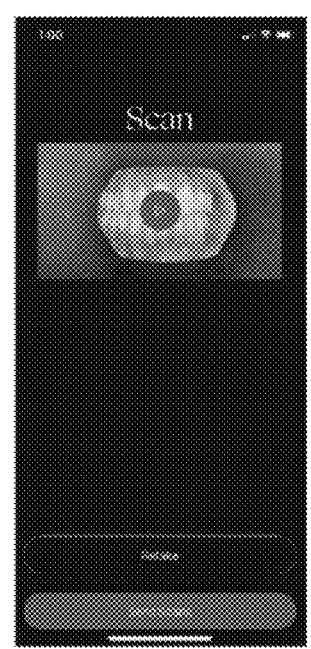
FIG. 18D schematically illustrates an intraoral video that may be sent to a dentist using a patient-side remote dental monitoring software application, in accordance with some embodiments.

Once the patient completes all selfie scans as shown in FIG. 18A, the selfie scan GUI may provide a scan complete notification as illustrated in FIG. 18B. As shown in FIG. 18C and FIG. 18D, the scan GUI may be configured to display the plurality of intraoral images or videos taken by the patient in accordance with the instructions provided by the scan GUI. In some cases, the scan GUI may provide a first option for the patient to retake one or more of the plurality of intraoral images or videos. In other cases, the scan GUI may provide a second option for the patient to send the scans to the dentist or caregiver via the chat application described elsewhere herein.

Caregiver GUI

In another aspect, the systems and methods of the present disclosure provide a practitioner-side software application comprising a caregiver user interface that allows a caregiver to interact with the patients remotely and to view the milestone and selfie scans captured by patients using the patient graphical user interface described herein. In some embodiments, the dentist application may be configured to permit the dentist to visually compare milestone and selfie scans for each of one or more patients. In some embodiments, one or more of the milestone or selfie scans can be sorted or filtered based on a patient's treatment or scan timeline.

Figure 19A:
FIGS. 19A and 19B schematically illustrate a user interface for a dentist to sign up for a practitioner-side remote dental monitoring software application, in accordance with some embodiments.
Figure 19B:
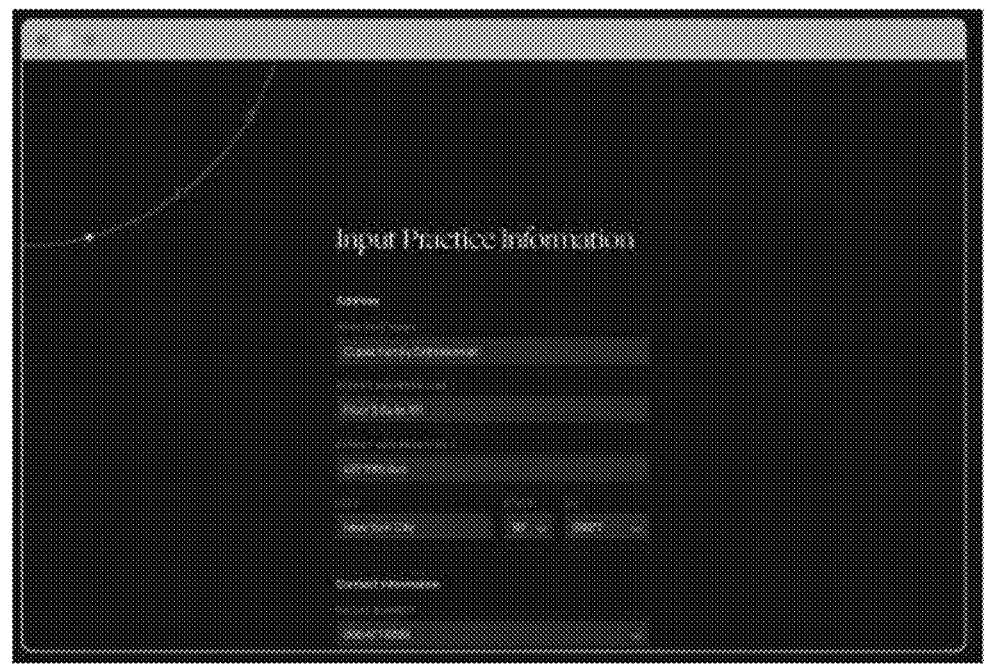
Figure 20A:
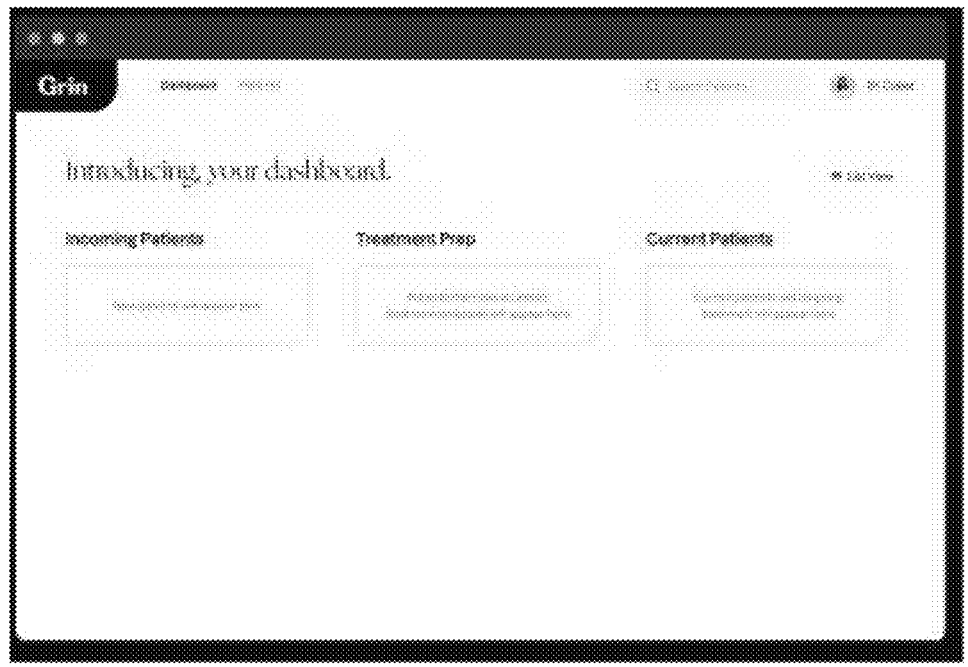
FIGS. 20A and 20B schematically illustrate a task dashboard for a practitioner-side remote dental monitoring software application, in accordance with some embodiments.
Figure 20B:
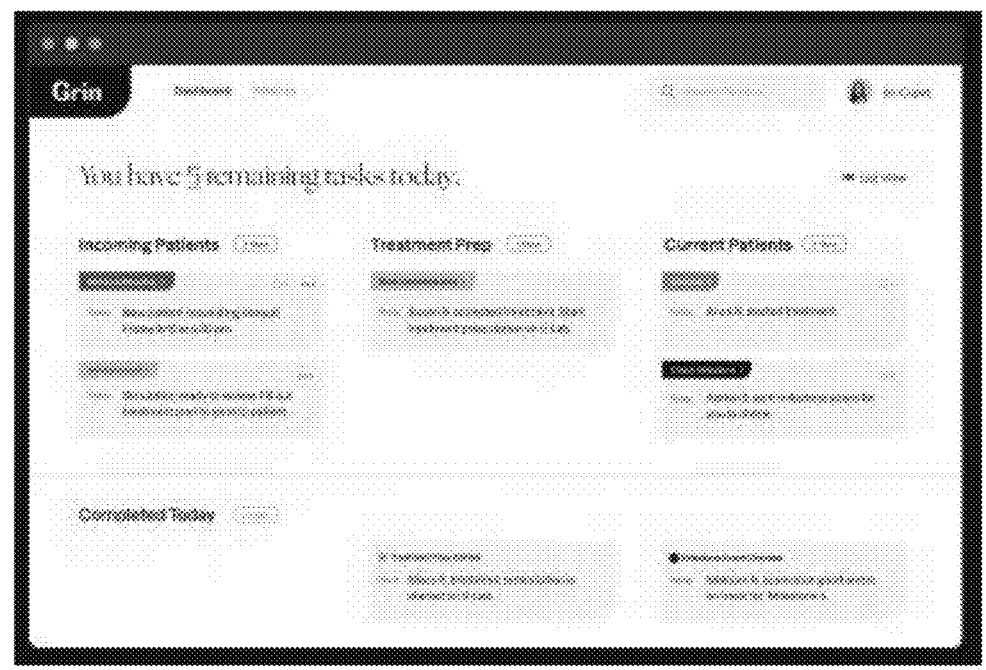

FIGS. 19A-19B show an exemplary onboarding page for a dentist or caregiver to create an account for dental remote monitoring applications. FIG. 20A shows an exemplary dashboard for a dentist to view information about incoming new patients, treatment preparation for patients that have accepted treatment proposals, and current patients with ongoing treatments. FIG. 20B shows the exemplary dashboard of FIG. 20A populated with tasks for the dentist to complete. In some embodiments, the tasks may be grouped into tasks for incoming patients, tasks for treatment preparation, tasks for current patients, and tasks completed today. The populated dashboard may provide the dentist with scheduling alerts to inform the dentist of new patients who have requested a consultation for dental treatment. The populated dashboard may also provide the dentist with a notice to send a proposal for dental treatment to new incoming patients. The populated dashboard may also provide the dentist with a notice that a simulation of a proposed treatment is ready for review, and that a treatment plan should be sent to the patient for review. The populated dashboard may also provide the dentist with a notice that a patient has accepted a treatment, and that the dentist should start treatment prescription. The populated dashboard may also provide the dentist with information about current patients. For example, the populated dashboard may provide the dentist with a notice that a current patient has started a treatment, or that a current patient has completed and sent milestone scans for the dentist to review. The populated dashboard may also provide the dentist with a notice that a current patient is on track with a treatment plan, and a notice that one or more milestone scans are ready to be checked. The populated dashboard may also provide the dentist with information about completed tasks (e.g., treatment prescription started for a new patient, or milestone scans checked for a current patient).

Figure 21A:
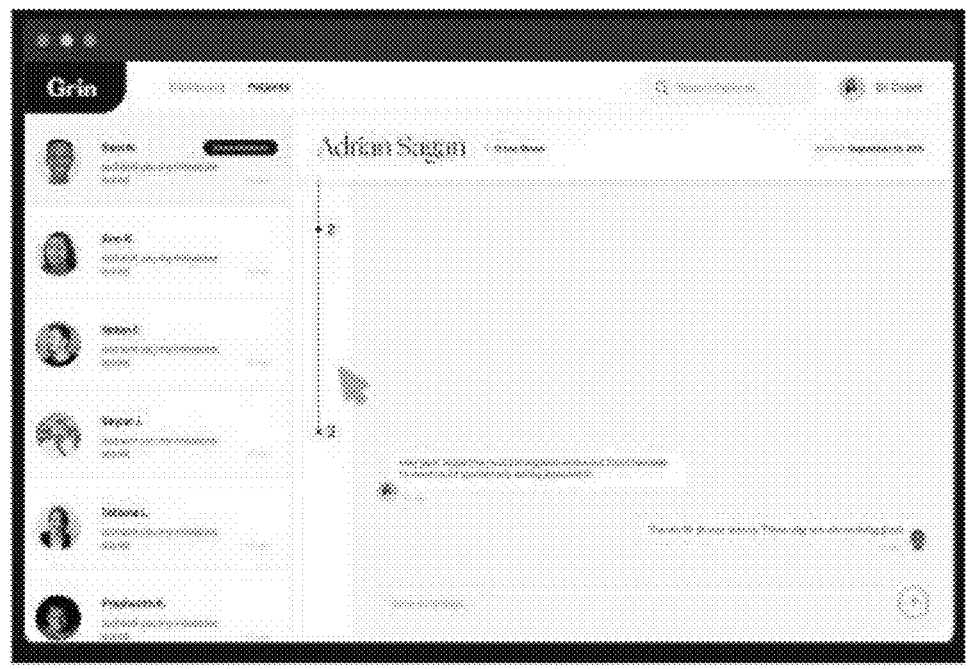
FIGS. 21A, 21B, and 22A schematically illustrate a chat user interface for a practitioner-side remote dental monitoring software application, in accordance with some embodiments.

FIG. 21A shows an exemplary dentist app GUI of a first patient tab that allows a caregiver to view previous patient chats and to converse with a patient via the chat interface. The GUI may provide a list of conversations with different patients for the dentist to access. When the dentist selects a patient from the patient tab, the GUI may be configured to display a chat interface comprising one or more messages between the dentist and the selected patient. The chat interface may provide a progress bar that shows how many milestones the patient has completed for the patient's current dental treatment plan.

Figure 21B:
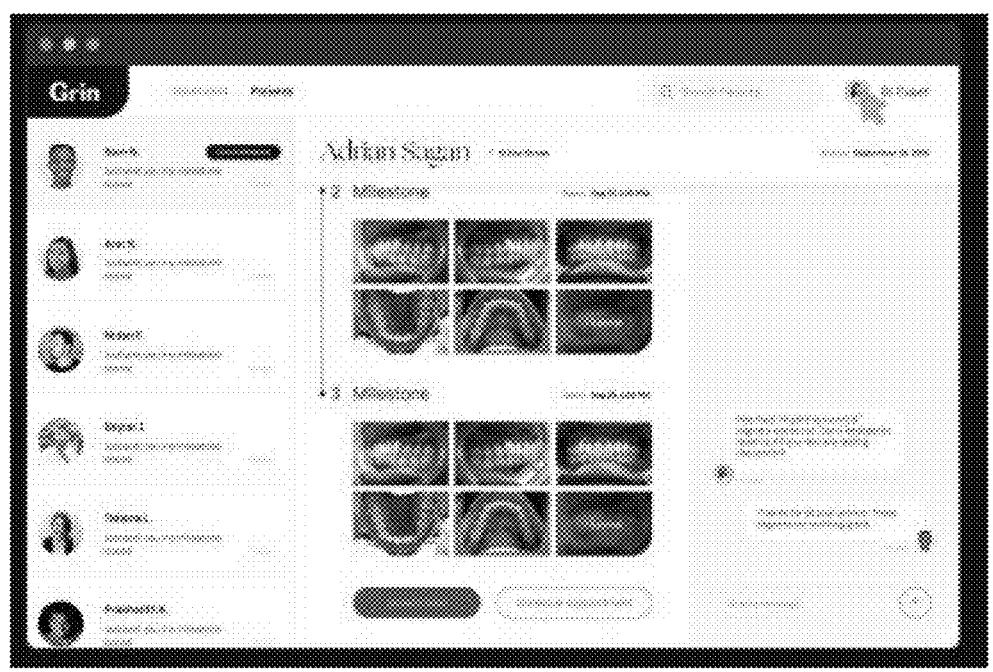

FIG. 21B shows an interactive chat interface between the dentist and a selected patient. The chat interface may be configured to display one or more intraoral scans taken by the patient for each milestone of the treatment plan. The chat interface may be configured to permit the dentist to view the individual milestone scans sent by the patient. The chat interface may be configured to provide the dentist with a first button to indicate that the milestone scans look good and that the patient is on track with the dental treatment plan. The chat interface may be configured to provide the dentist with a second button to schedule an appointment with the patient.

Figure 22A:
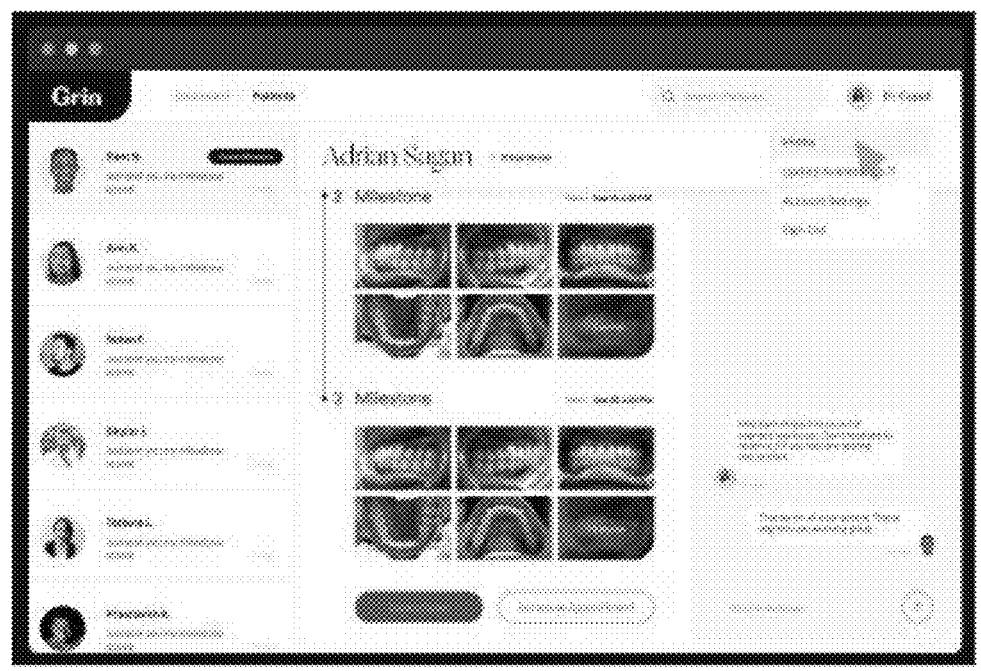
Figure 22B:
FIG. 22B schematically illustrates a dentist profile page, in accordance with some embodiments.

FIG. 22A shows a drop down menu that may be provided for the dentist to access a dentist profile page. The drop down menu may also provide the dentist with an option to update his or her availability and to access account settings. FIG. 22B shows an exemplary profile page for the dentist. The profile page may display the name of the dentist, the credentials of the dentist, contact information, address information, and hours of operation. The profile page may permit the dentist to update his or her availability. The profile page may also display when the dentist joined the remote monitoring platform, how many consultations the dentist performed, how many patients the dentist currently has, and how many treatments the dentist completed.

Scan Review

In some embodiments, the practitioner-side software application may comprise a scan review user interface that allows a practitioner or caregiver to remotely review one or more dental scans obtained by a patient. The one or more dental scans may comprise a video and/or a plurality of images of one or more intraoral regions or features of a patient. In some cases, the video and/or the plurality of images may correspond to different views of a patient's dental features or structures. The scan review user interface may permit remote consultation by allowing practitioners to review scans and provide live commentary or annotations while viewing one or more intraoral images or videos taken by the patient. In any of the embodiments described herein, the scan review performed by a practitioner may comprise a recording (e.g., an audio and/or video recording) of the practitioner as the practitioner views and/or provides commentary or feedback on the one or more intraoral images or videos. The recording may be captured using the scan review user interface and may be transmitted or provided to the dental patient who captured the one or more intraoral images or videos using the patient-side user interfaces disclosed herein.

Figure 23A:
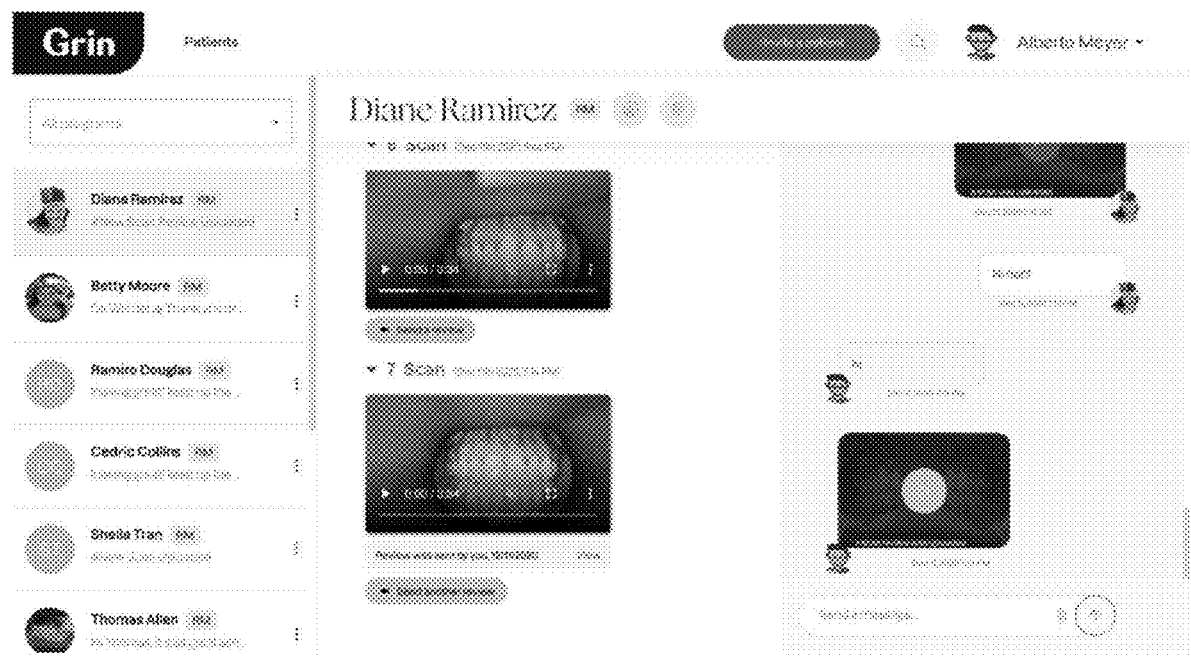
FIGS. 23A, 23B, 23C, 23D, 24A, and 24B schematically illustrate a user interface for a practitioner to review a patient's dental scans, in accordance with some embodiments.

As shown in FIG. 23A, the practitioner-side UI may be configured to display one or more dental scans taken by patient. The practitioner-side UI may provide a practitioner with an option to conduct and/or send a review of the one or more dental scans. The review of the one or more dental scans may comprise one or more annotations, visual commentary (e.g., movement of a pointer or a cursor to indicate one or more features or regions of interest), and/or audio commentary on the one or more dental scans. The one or more annotations and/or the visual or audio commentary may be provided by the practitioner as the practitioner reviews the dental scans received from the patient. In some cases, the one or more annotations may be manually created or provided by the practitioner as the practitioner reviews the dental scans. In other cases, the practitioner may select one or more annotations from a library of annotations and manually place or position the annotations onto a desired feature or region that appears in the dental scans.

In some cases, the one or more annotations may comprise, for example, a bounding box that is generated around one or more regions or features of the dental scans. In some cases, the one or more annotations may comprise a zero-dimensional feature that is generated within the dental scans. In some instances, the zero-dimensional feature may comprise a dot. In some cases, the one or more annotations may comprise a one-dimensional feature that is generated within the dental scans. In some instances, the one-dimensional feature may comprise a line, a line segment, or a broken line comprising two or more line segments. In some cases, the one-dimensional feature may comprise a linear portion. In some cases, the one-dimensional feature may comprise a curved portion. In some cases, the one or more annotations may comprise a two-dimensional feature that is generated within the dental scans. In some cases, the two-dimensional feature may comprise a circle, an ellipse, or a polygon with three or more sides. Alternatively, the two-dimensional feature may comprise any amorphous, irregular, indefinite, random, or arbitrary shape. Such amorphous, irregular, indefinite, random, or arbitrary shape may be drawn or generated by the practitioner or caregiver using one or more input devices (e.g., a computer mouse, a laptop trackpad, or a mobile device touch screen). In some cases, two or more sides of the polygon may comprise a same length. In other cases, two or more sides of the polygon may comprise different lengths. In some cases, the two-dimensional feature may comprise a shape with two or more sides having different lengths or different curvatures. In some cases, the two-dimensional feature may comprise a shape with one or more linear portions and/or one or more curved portions. In some cases, the two-dimensional feature may comprise an amorphous shape that does not correspond to a circle, an ellipse, or a polygon. In some cases, the two-dimensional feature may comprise an arbitrary shape that is drawn or generated by an annotator (e.g., the practitioner reviewing the dental scans). In some cases, the one or more annotations may comprise a textual, numerical, or visual annotation to the dental scans.

FIGS. 25A, 25B, 25C, and 25D illustrate various examples of annotations that may be provided by a practitioner reviewing a dental scan. In some cases, the annotations may comprise, for example, a predetermined shape 2501 (e.g., a circle or a square) that may be placed or overlaid on one or more dental features or dental regions appearing in a dental scan. The predetermined shape 2501 may be positioned or repositioned using a click to place or drag and drop operation. In other cases, the annotations may comprise, for example, any manually drawn shape 2502 generated by the practitioner using an input device such as a computer mouse, a mobile device touchscreen, or a laptop touchpad. The manually drawn shape 2502 may comprise any amorphous, irregular, indefinite, random, or arbitrary shape. In some alternative embodiments, the annotations may comprise an arrow 2503 or a text-based annotation 2504 that is placed on or near one or more dental features or regions appearing in a dental scan.

In some embodiments, the one or more annotations may be provided to identify, highlight, point out, or mark a particular feature or region that appears in the dental scans. In some cases, the scan review interface may be configured to permit the practitioner to manually point out and/or track one or more features or regions of interest as the scan review progresses (e.g., by using a virtual cursor or pointer). In other cases, the remote monitoring platform may be configured to automatically update a position and/or an orientation of the one or more annotations to continuously track the features or regions of interest appearing within the dental scans as the scan review progresses. Such automatic tracking of features or regions may be implemented using any of the artificial intelligence or machine learning algorithm disclosed herein.

Figure 26A:
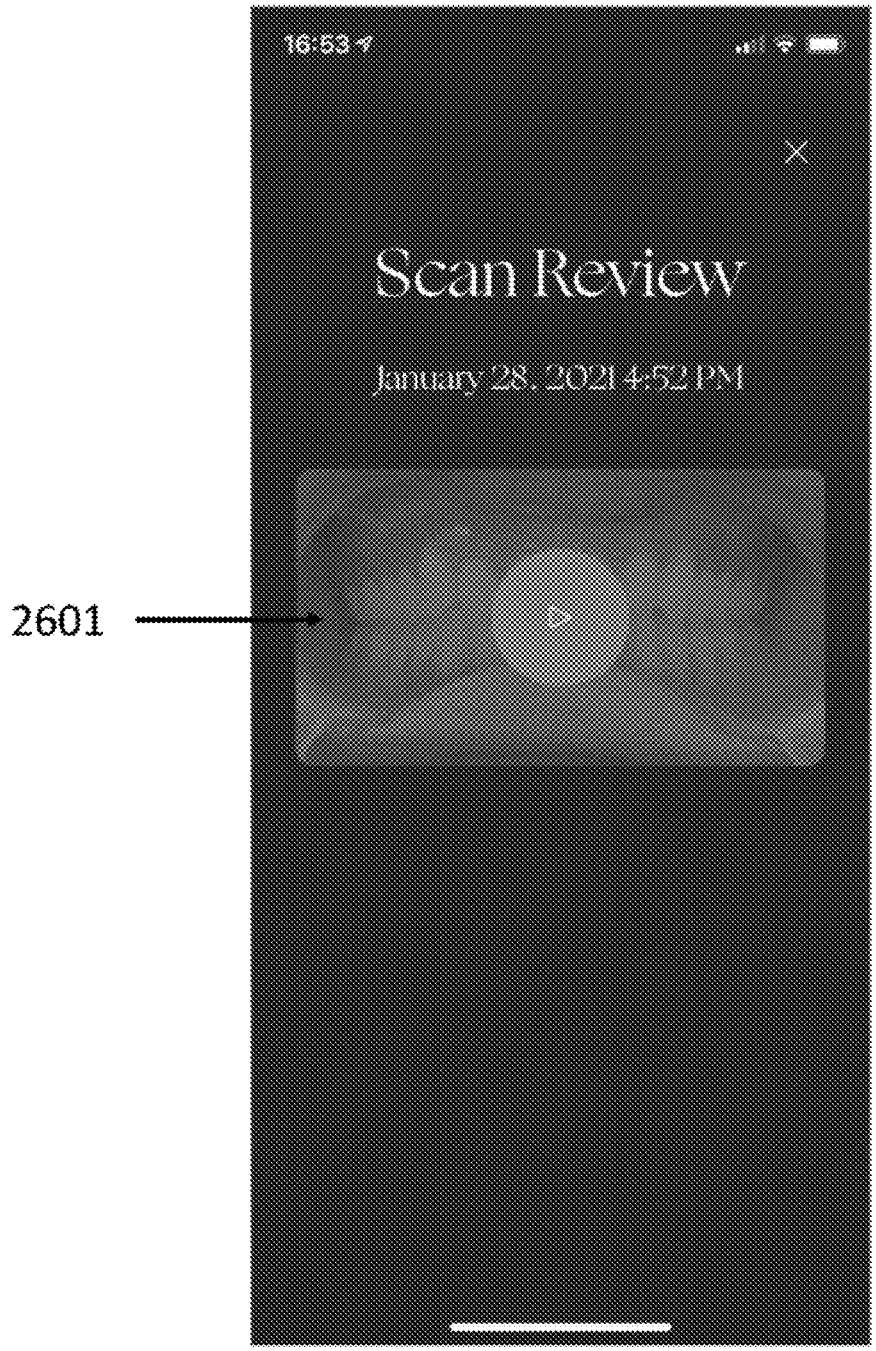
FIGS. 26A, 26B, 27, and 28 schematically illustrate a text box containing a transcription of audio commentary provided by a practitioner during a scan review.
Figure 26B:
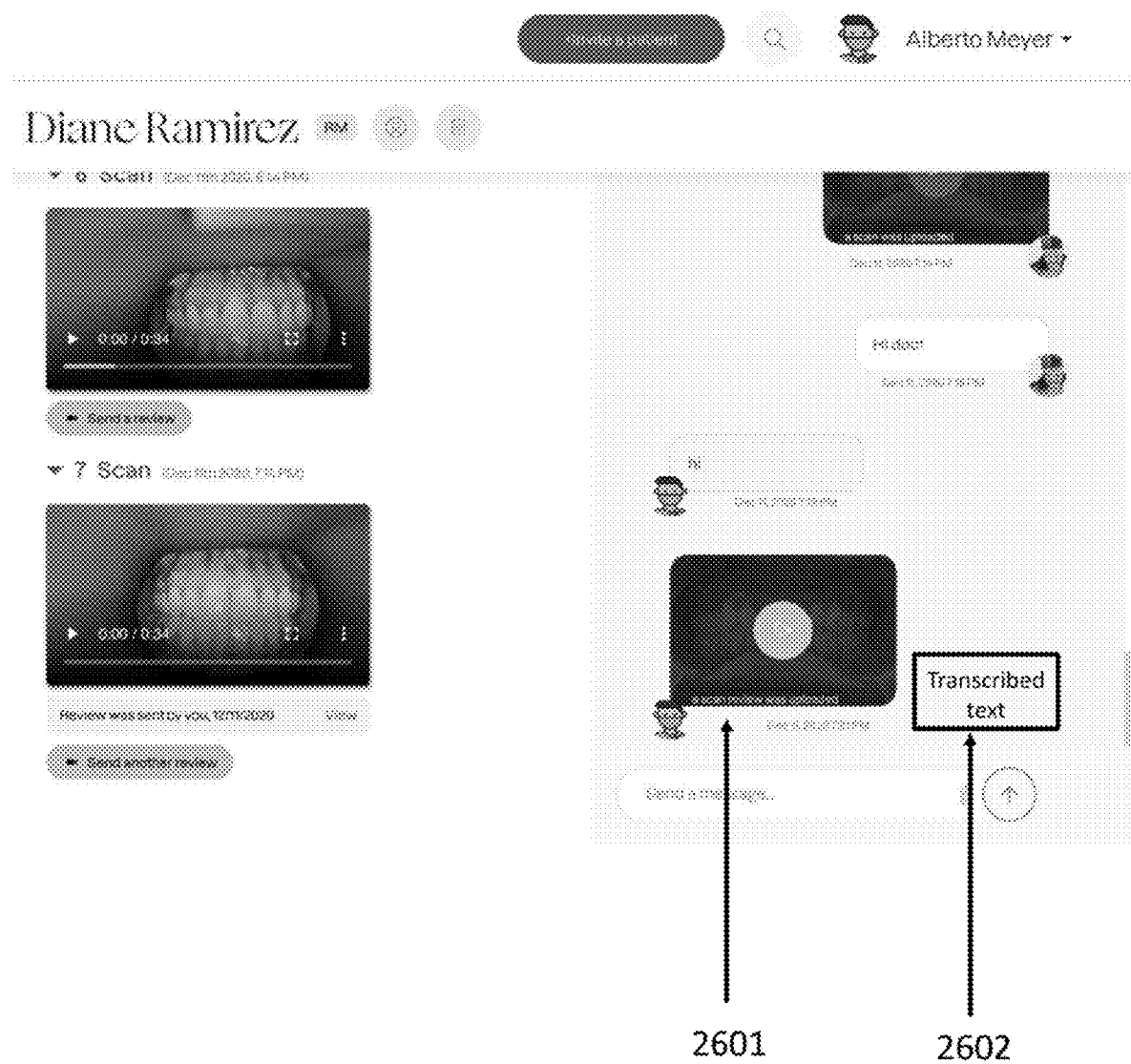
Figure 27:
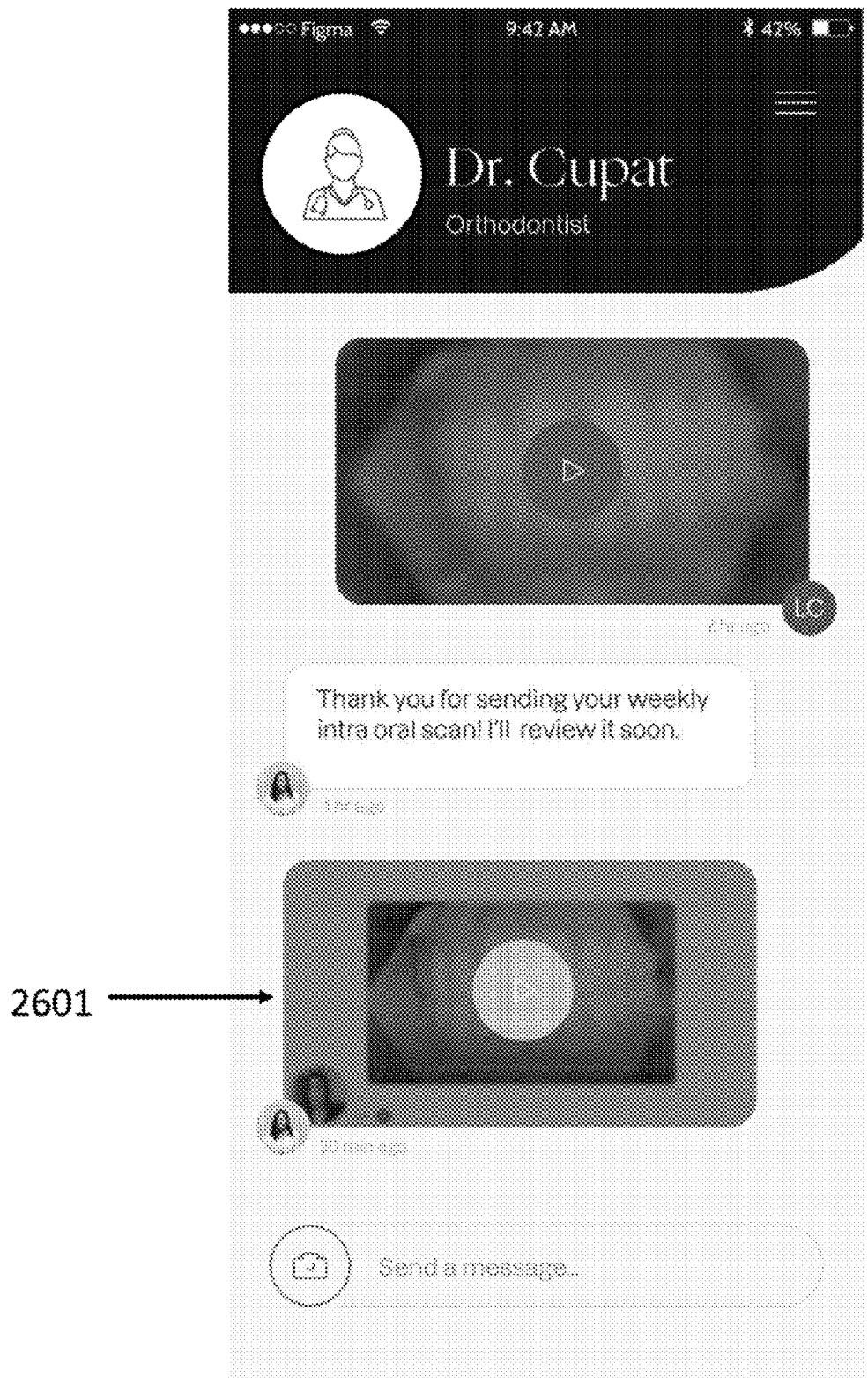
Figure 28:
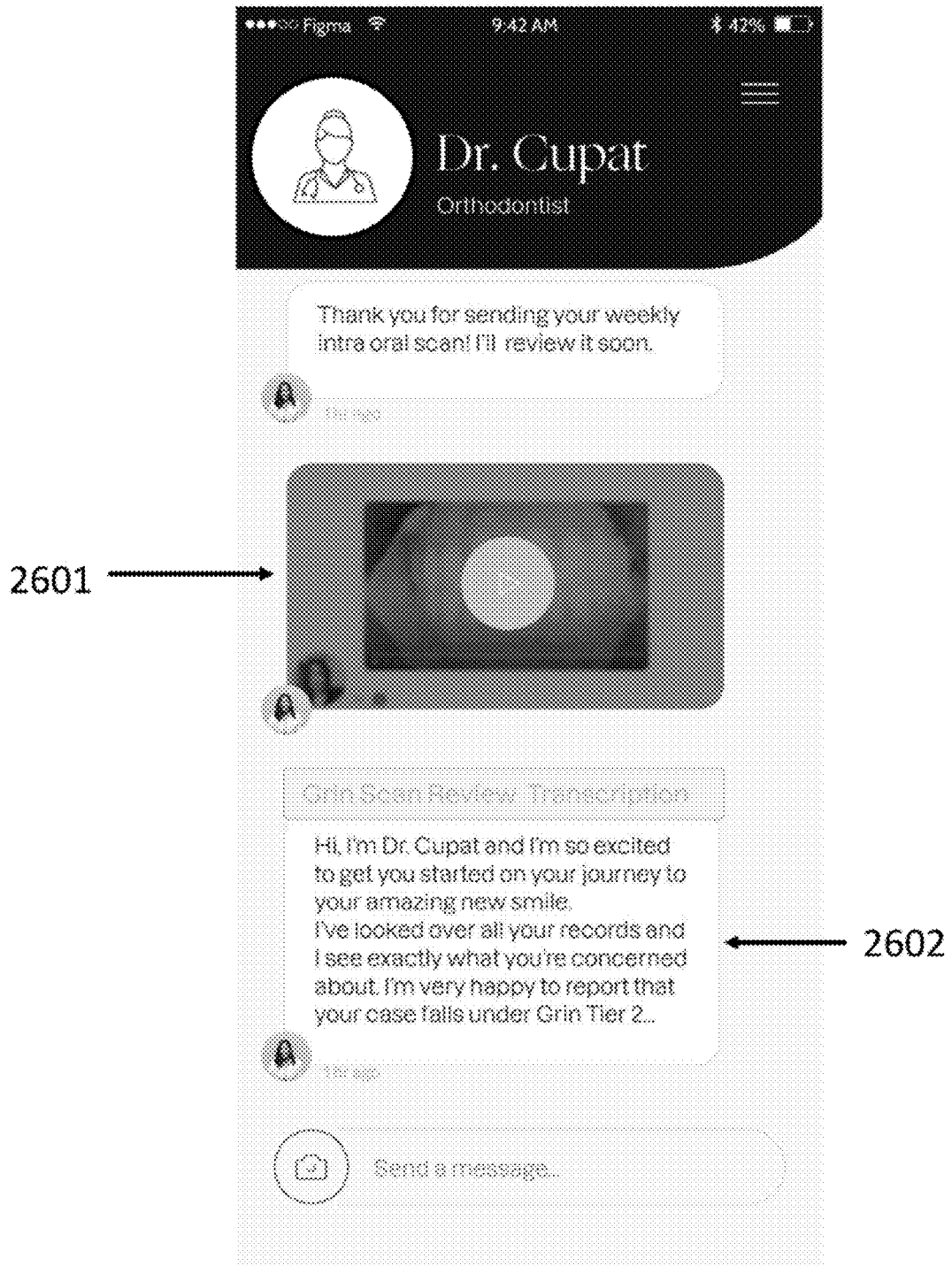

In some embodiments, the practitioner may provide audio commentary as the practitioner reviews the one or more dental scans. The audio commentary may be provided alone or in combination with other forms of commentary (e.g., visual commentary or annotations). In some cases, the audio commentary may be transcribed into a textual format. The audio commentary may be transcribed into a textual format using, for example, a speech-to-text engine, a phonetics-based speech analytics engine, or natural language processing (NLP). In some instances, NLP may be implemented using one or more artificial intelligence or machine learning algorithms configured to analyze speech and text. The machine learning algorithms may comprise any of the machine learning algorithms described elsewhere herein. The transcribed text and the video recording of the scan review performed by the practitioner may be provided to the patient through a chat interface. As described elsewhere herein, the chat interface may enable remote communications between the practitioner and the patient. In some cases, the transcribed text may appear in a text box or as a text message in the chat interface, as shown in FIG. 26B.

Figure 23B:
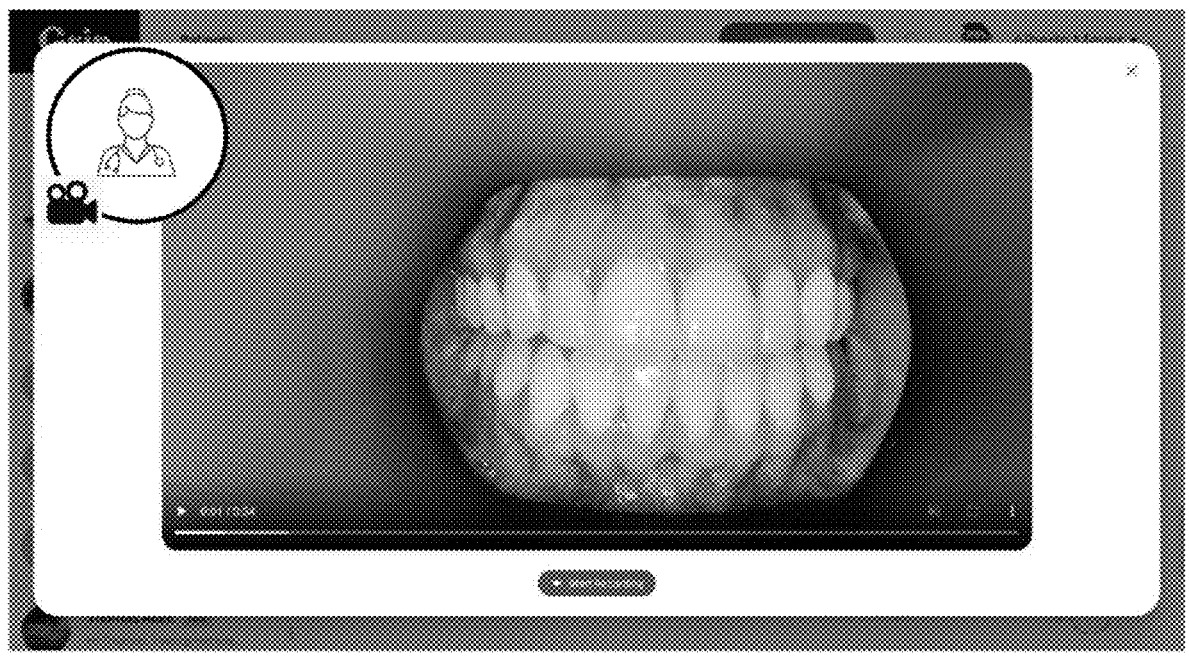
Figure 23C:
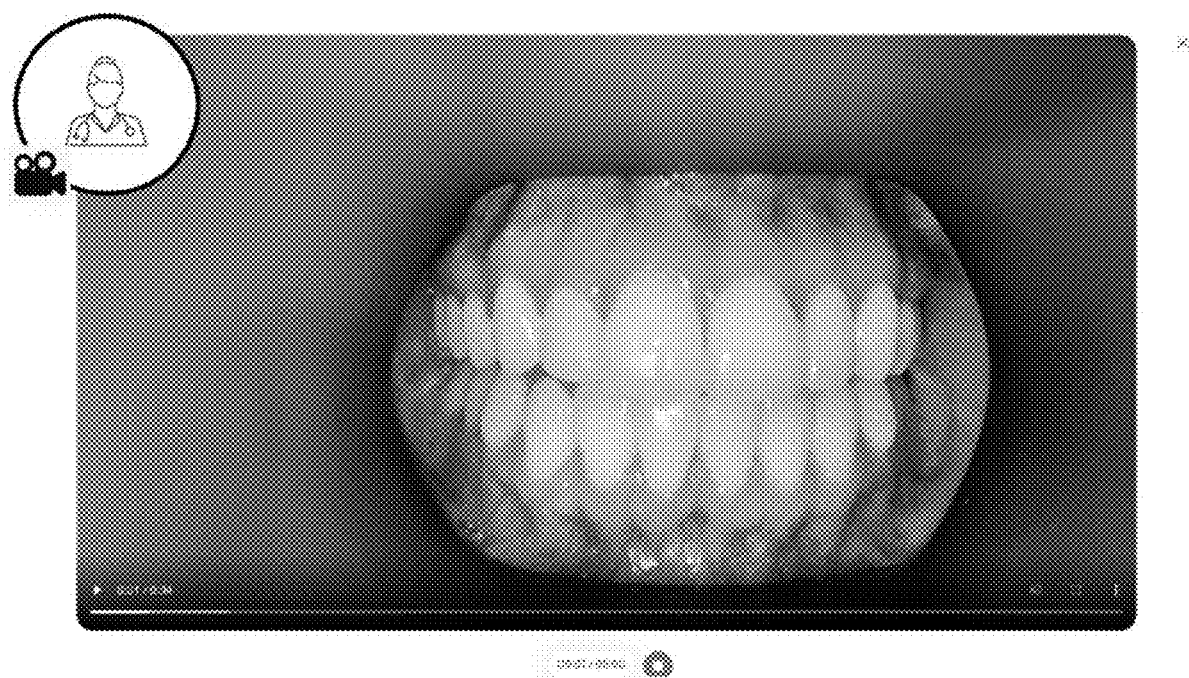
Figure 23D:
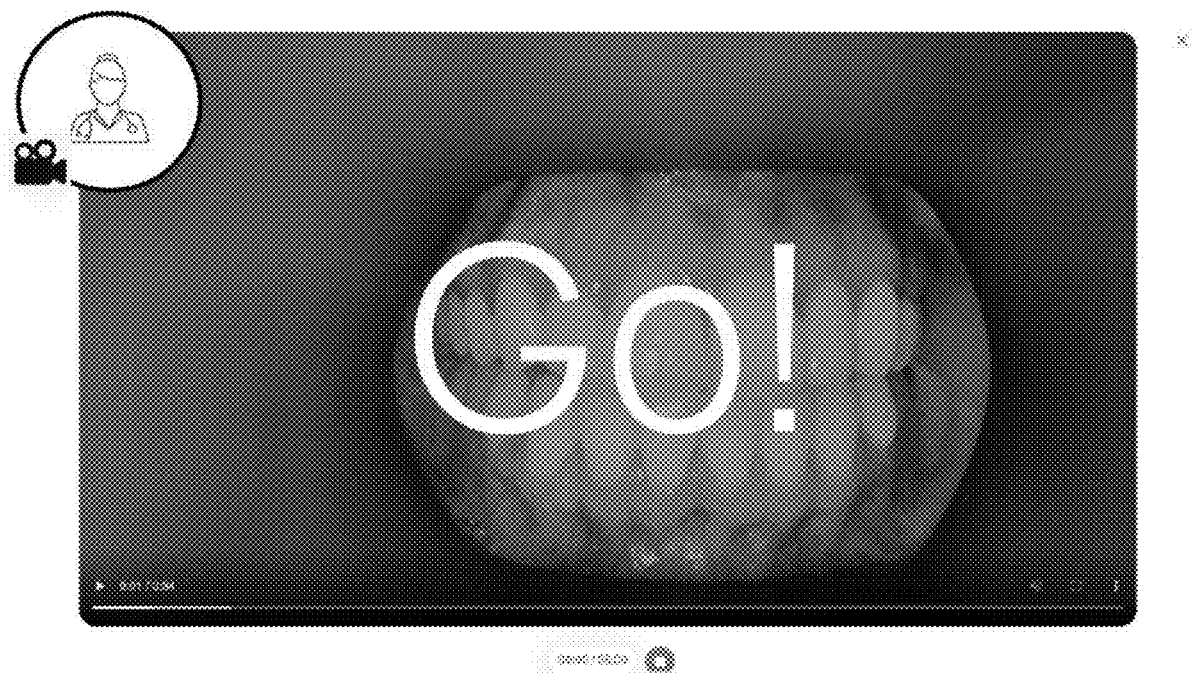

As shown in FIG. 23B, FIG. 23C, and FIG. 23D, once a practitioner selects a particular dental scan to review, the practitioner-side UI may provide the practitioner with an enlarged view of the dental scan. The UI may also permit the practitioner to view (e.g., watch or play) the dental scan and begin recording commentary or providing annotations concurrently as the dental scan is being viewed. In some cases, the UI may also permit the practitioner to initiate a live video stream of the practitioner as the practitioner is providing or recording the commentary or annotations.

Figure 24A:
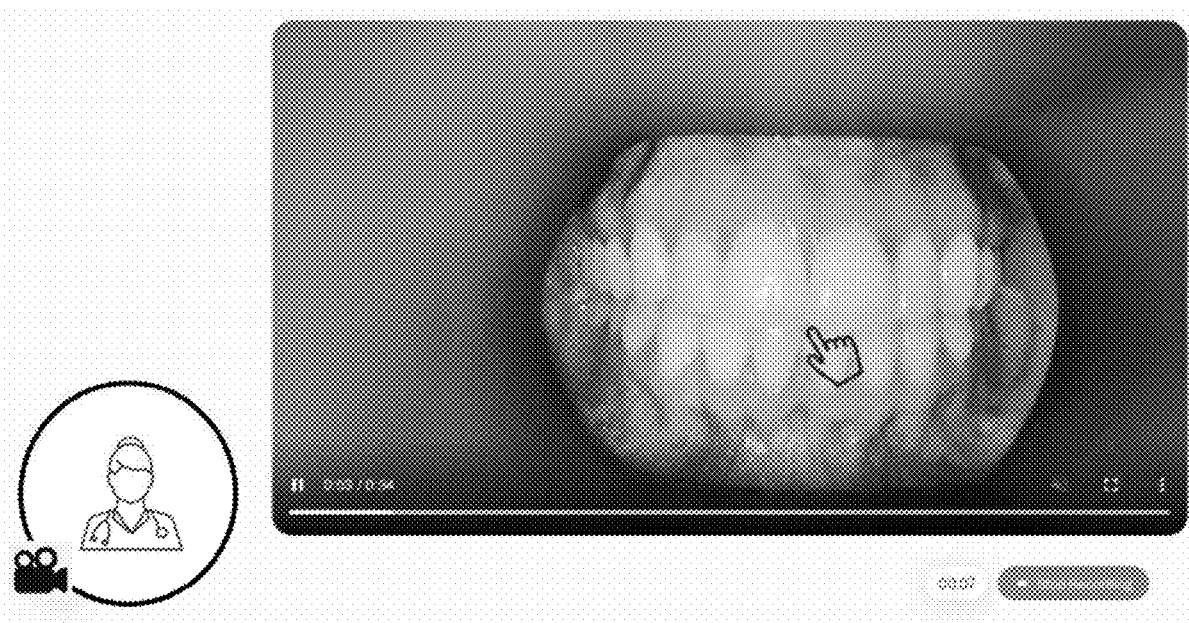
Figure 24B:
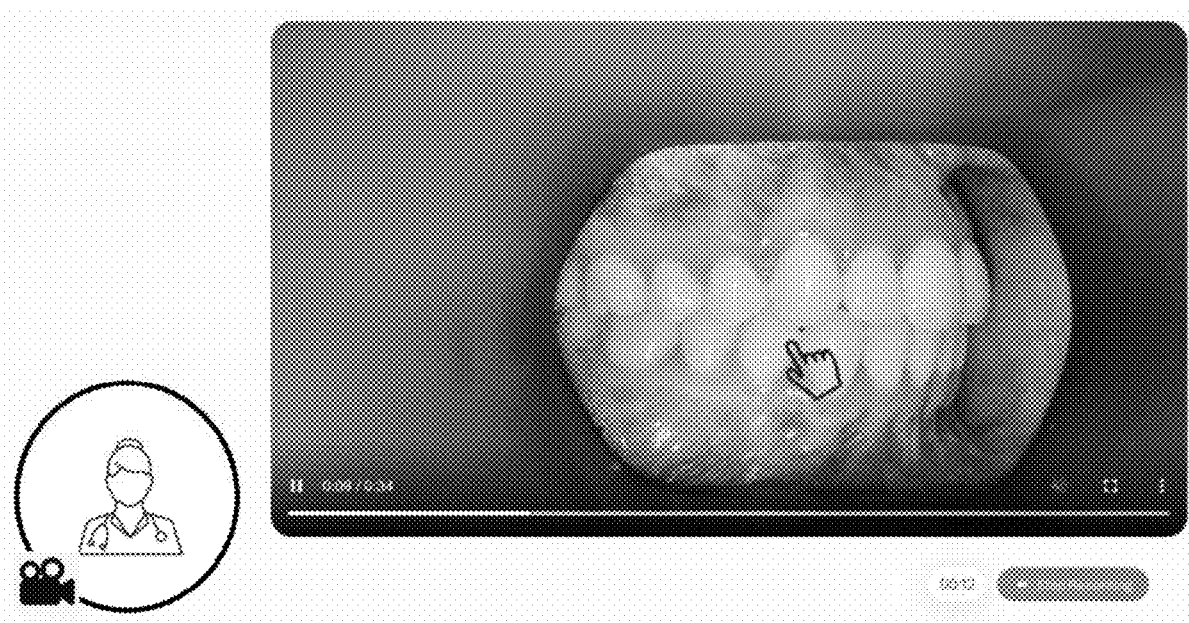
Figure 25A:
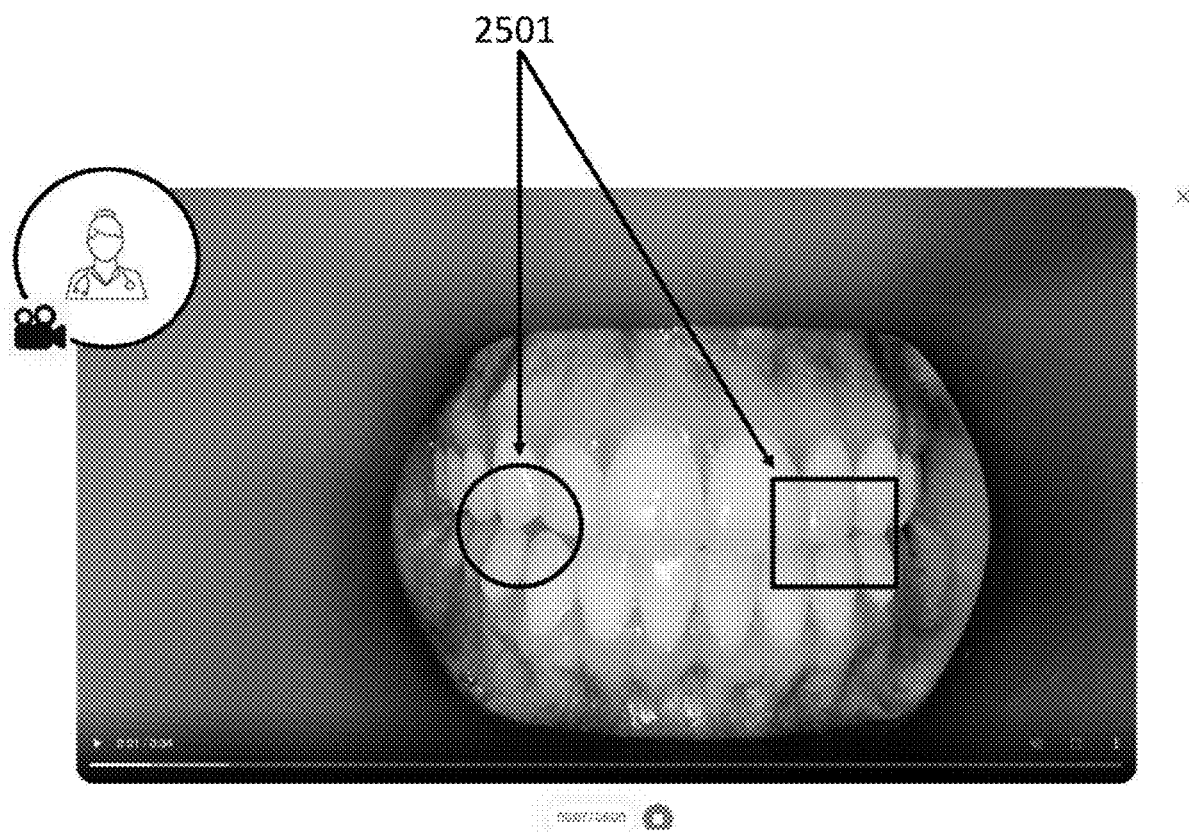
FIGS. 25A, 25B, 25C, and 25D schematically illustrate various examples of annotations that may be provided by a practitioner during a scan review.
Figure 25B:
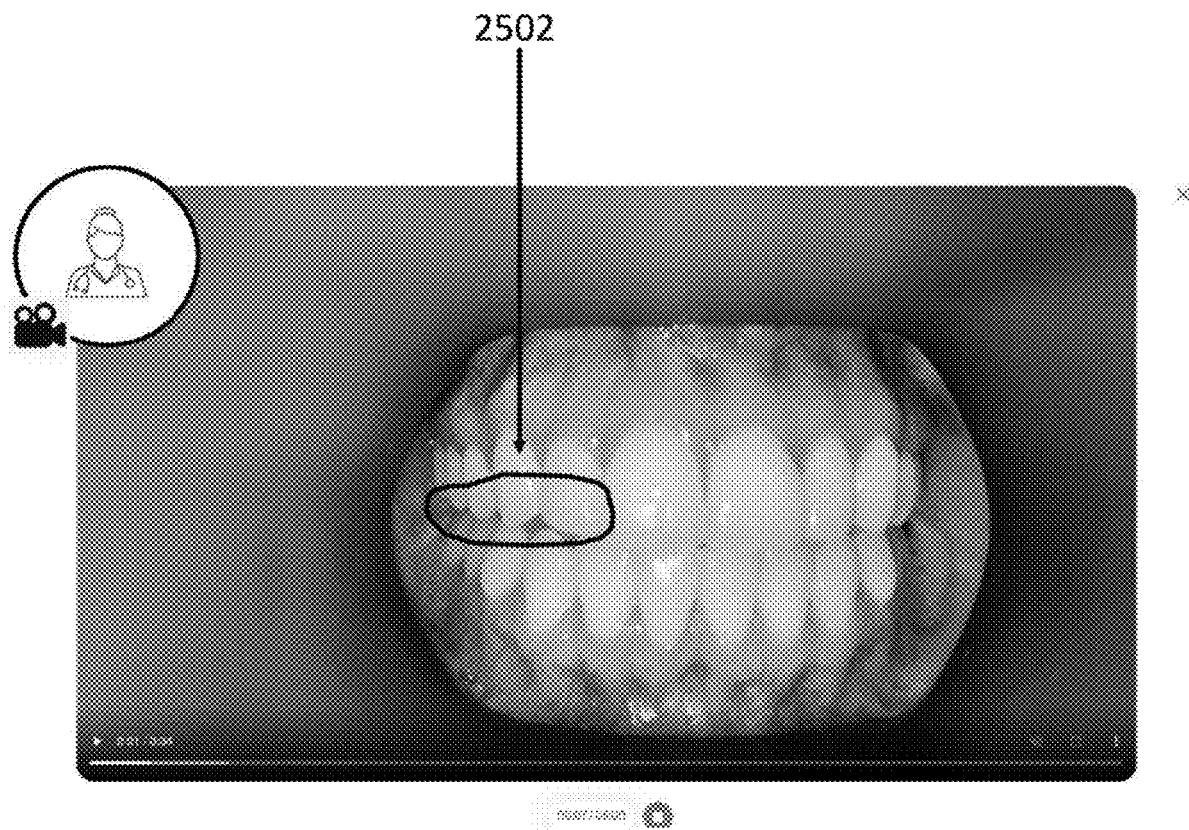
Figure 25C:
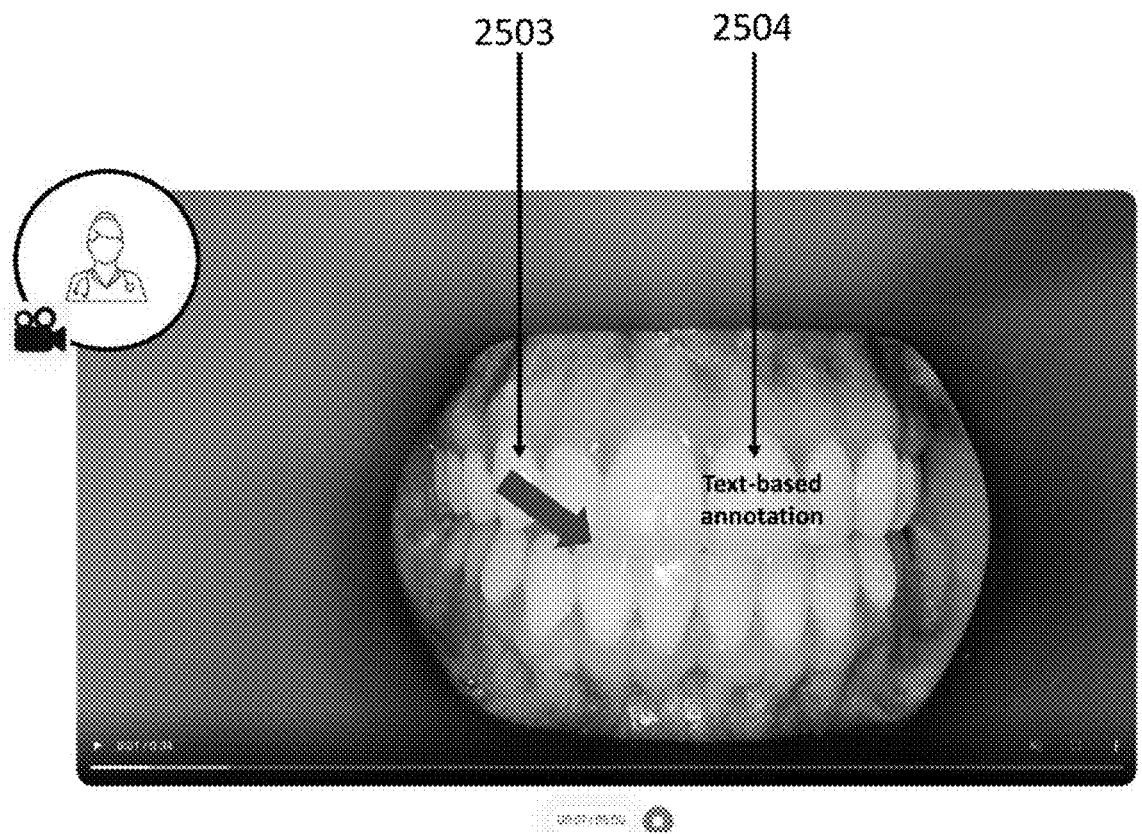
Figure 25D:
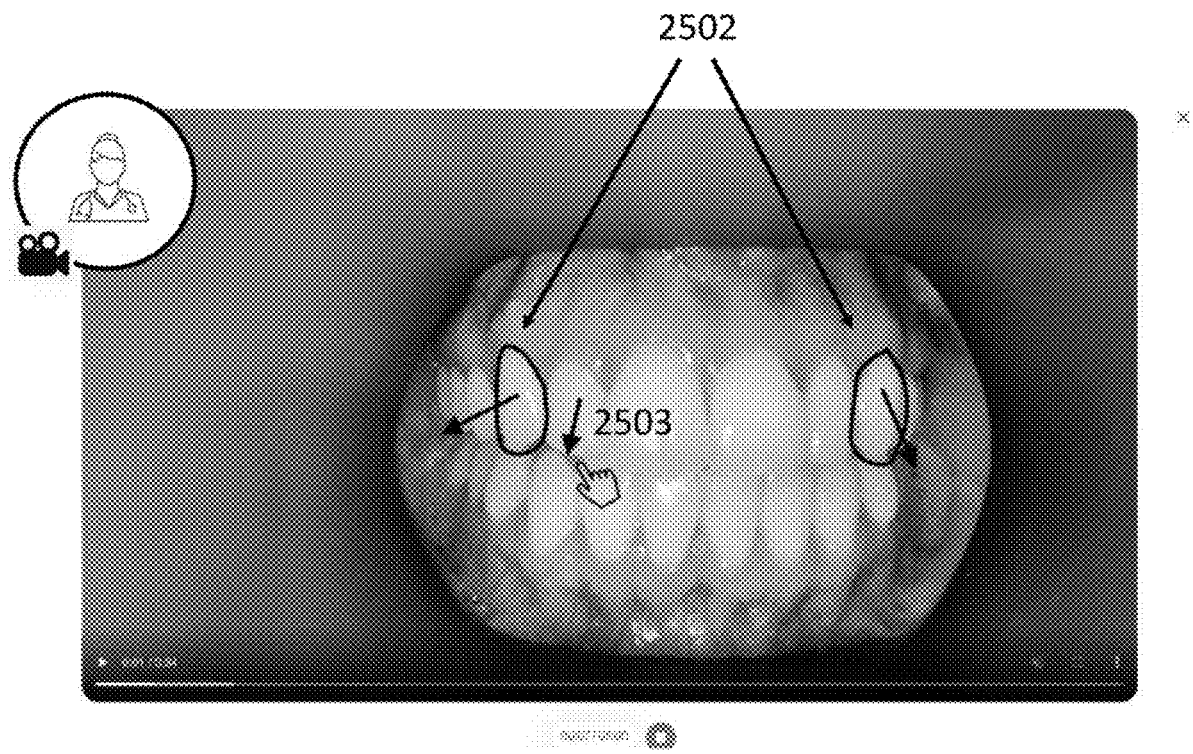

FIG. 24A and FIG. 24B illustrate an example of a dental scan review being recorded. In some cases, the UI may be configured such that the practitioner reviewing the dental scan can control a pointer to indicate one or more features or regions of interest in the dental scans as the practitioner records the review of the dental scan. In some cases, the UI may permit the practitioner to provide one or more annotations (or other forms of visual or audio commentary) to the dental scans as the practitioner records the review of the dental scan. Once a practitioner concludes the review of the dental scan, the practitioner can stop the recording, and the practitioner-side UI may be configured to send the recorded review to the patient (e.g., via the chat interface between the practitioner and the patient). As shown in FIG. 26A, FIG. 26B, FIG. 27, and FIG. 28, the patient-side UI may be configured to display the recorded dental scan review 2601 for the patient to view. The recorded dental scan review 2601 may be displayed within a chat interface. In some cases, the patient-side UI may be further configured to display a transcription 2602 of any audio commentary provided by the practitioner during and/or after the practitioner's review of the patient's dental scans.

Methods of Capturing a Milestone Scan

In an aspect, the present disclosure provides methods of capturing a milestone scan of a patient using a mobile device and the intraoral adapter provided herein. In some embodiments, the method comprises one or more of: capturing a first milestone scan; capturing a second milestone scan; capturing a third milestone scan; capturing a fourth milestone scan; capturing a fifth milestone scan; capturing a first milestone selfie scan; capturing a second milestone selfie scan; and capturing a third milestone selfie scan.

In some embodiments, the method comprises one or more of: prompting the patient to record the milestone scan; prompting the patient to orient the mobile device horizontally; prompting the patient to attach the intraoral adaptor to the mobile device; prompting the patient to place the intraoral adaptor over their mouth; prompting the patient to face a mirror; prompting the patient to bite down and smile; capturing a first milestone scan; prompting the patient to turn to their right; capturing a second milestone scan; prompting the patient to turn to the left; capturing a third milestone scan; prompting the patient to open their mouth and point the intraoral adaptor at their bottom teeth; capturing a fourth milestone scan; prompting the patient to open their mouth and point the intraoral adaptor at their top teeth; capturing a fifth milestone scan; prompting the patient to exit the scan mode; prompting the patient to capture a milestone selfie scan of the front of their face; capturing a first milestone selfie scan; prompting the patient to capture a milestone selfie scan of the right side of their face; capturing a second milestone selfie scan; prompting the patient to capture a milestone selfie scan of the left side of their face; capturing a third milestone selfie scan; prompting the patient to confirm their milestone scans; and notifying the patient that the milestone scans have been sent.

In some embodiments, one or more of the first milestone scan, the second milestone scan, the third milestone scan, the fourth milestone scan, the fifth milestone scan, the first selfie scan, the second selfie scan, and the third selfie scan may comprise a single image. In some embodiments, one or more of the first milestone scan, the second milestone scan, the third milestone scan, the fourth milestone scan, the fifth milestone scan, the first selfie scan, the second selfie scan, and the third selfie scan may comprise a plurality of images. In some embodiments, one or more of the first milestone scan, the second milestone scan, the third milestone scan, the fourth milestone scan, the fifth milestone scan, the first selfie scan, the second selfie scan, and the third selfie scan may comprise a video or a plurality of videos. In some embodiments, one or more of the first milestone scan, the second milestone scan, the third milestone scan, the fourth milestone scan, the fifth milestone scan, the first selfie scan, the second selfie scan, and the third selfie scan may further comprise audio data.

Computer Systems

Figure 4:
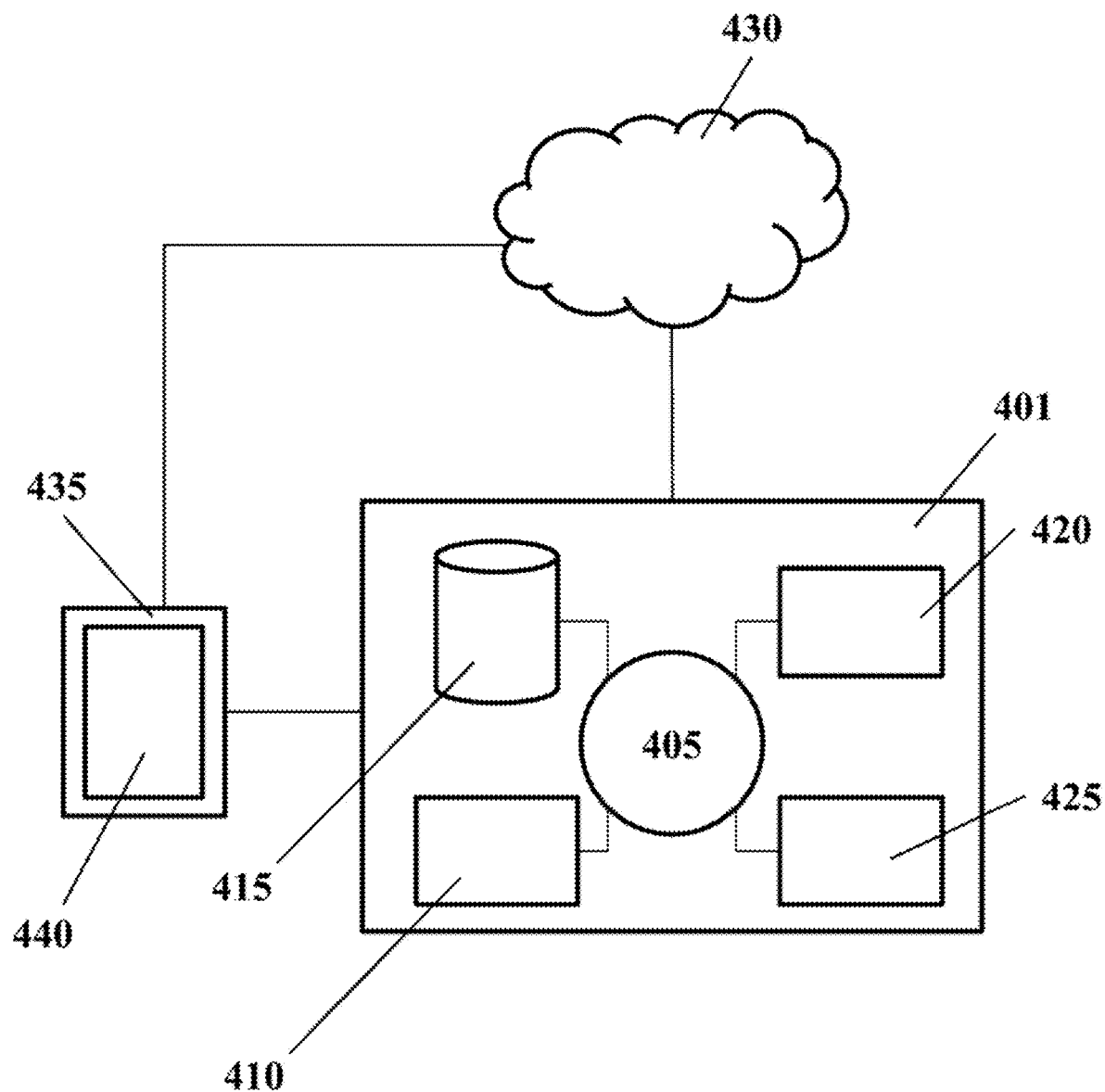
FIG. 4 schematically illustrates a computer system that is programmed or otherwise configured to implement methods provided herein.

In an aspect, the present disclosure provides computer systems that are programmed or otherwise configured to implement methods of the disclosure. FIG. 4 shows a computer system 401 that is programmed or otherwise configured to implement a method for remote dental monitoring. The computer system 401 may be configured to, for example, process a plurality of intraoral images captured using the camera of the mobile device, and determine a dental condition of the subject based at least in part on the plurality of intraoral images. The computer system 401 may be configured to (i) predict a movement of one or more teeth of the subject, (ii) identify enamel wear patterns, (iii) create or modify a dental treatment plan, or (iv) generate or update an electronic medical record associated with the dental condition of the subject. The computer system 401 may be configured to generate a three-dimensional (3D) model of a dental structure of the subject based at least in part on the plurality of intraoral images, and determine a dental condition of the subject based at least in part on the three-dimensional model. The computer system 401 can be an electronic device of a user or a computer system that is remotely located with respect to the electronic device. The electronic device can be a mobile electronic device.

The computer system 401 may include a central processing unit (CPU, also "processor" and "computer processor" herein) 405, which can be a single core or multi core processor, or a plurality of processors for parallel processing. The computer system 401 also includes memory or memory location 410 (e.g., random-access memory, read-only memory, flash memory), electronic storage unit 415 (e.g., hard disk), communication interface 420 (e.g., network adapter) for communicating with one or more other systems, and peripheral devices 425, such as cache, other memory, data storage and/or electronic display adapters. The memory 410, storage unit 415, interface 420 and peripheral devices 425 are in communication with the CPU 405 through a communication bus (solid lines), such as a motherboard. The storage unit 415 can be a data storage unit (or data repository) for storing data. The computer system 401 can be operatively coupled to a computer network ("network") 430 with the aid of the communication interface 420. The network 430 can be the Internet, an internet and/or extranet, or an intranet and/or extranet that is in communication with the Internet. The network 430 in some cases is a telecommunication and/or data network. The network 430 can include one or more computer servers, which can enable distributed computing, such as cloud computing. The network 430, in some cases with the aid of the computer system 401, can implement a peer-to-peer network, which may enable devices coupled to the computer system 401 to behave as a client or a server.

The CPU 405 can execute a sequence of machine-readable instructions, which can be embodied in a program or software. The instructions may be stored in a memory location, such as the memory 410. The instructions can be directed to the CPU 405, which can subsequently program or otherwise configure the CPU 405 to implement methods of the present disclosure. Examples of operations performed by the CPU 405 can include fetch, decode, execute, and writeback.

The CPU 405 can be part of a circuit, such as an integrated circuit. One or more other components of the system 401 can be included in the circuit. In some cases, the circuit is an application specific integrated circuit (ASIC).

The storage unit 415 can store files, such as drivers, libraries and saved programs. The storage unit 415 can store user data, e.g., user preferences and user programs. The computer system 401 in some cases can include one or more additional data storage units that are located external to the computer system 401 (e.g., on a remote server that is in communication with the computer system 401 through an intranet or the Internet).

The computer system 401 can communicate with one or more remote computer systems through the network 430. For instance, the computer system 401 can communicate with a remote computer system of a user (e.g., a subject, a dental patient, or a dentist). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 401 via the network 430.

Methods as described herein can be implemented by way of machine (e.g., computer processor) executable code stored on an electronic storage location of the computer system 401, such as, for example, on the memory 410 or electronic storage unit 415. The machine executable or machine readable code can be provided in the form of software. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media including, for example, optical or magnetic disks, or any storage devices in any computer(s) or the like, may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 401 can include or be in communication with an electronic display 435 that comprises a user interface (UI) 440 for providing, for example, a portal for a practitioner, a subject, or a dental patient to view one or more intraoral images or videos captured using a mobile device of the subject or the dental patient. In some cases, the user interface may provide a portal for a practitioner, a subject, or a dental patient to view one or more three-dimensional models of the subject's or dental patient's dental structure generated based on the one or more intraoral images captured using the mobile device. In some cases, the user interface may provide a portal for a practitioner, a subject, or a dental patient to view one or more treatment plans generated based on the one or more intraoral images and/or the one or more three-dimensional models of the subject's dental structure. The portal may be provided through an application programming interface (API). A user or entity can also interact with various elements in the portal via the UI. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 405. The algorithm can, for example, implement a method for remote dental monitoring. The method may comprise processing a plurality of intraoral images or videos captured using the camera of the mobile device, and determining a dental condition of the subject based at least in part on the plurality of intraoral images. In some cases, the method may comprise (i) predicting a movement of one or more teeth of the subject, (ii) identifying enamel wear patterns, (iii) creating or modifying a dental treatment plan, or (iv) generating or updating an electronic medical record associated with the dental condition of the subject, based at least in part on the plurality of intraoral images. In some cases, the method may comprise using the intraoral images or videos to generate a three-dimensional (3D) model of a dental structure of the subject, and determining a dental condition of the subject based at least in part on the three-dimensional model.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A computer-implemented method for remote dental monitoring, the method comprising:
    (a) providing a patient portal for one or more patients to remotely communicate with a caregiver, wherein the patient portal comprises a graphical user interface that is configured to aid the one or more patients in capturing one or more dental scans, wherein the one or more dental scans comprise (i) one or more intraoral videos and (ii) a plurality of images derived from the one or more intraoral videos; and
    (b) providing the one or more dental scans to the caregiver for an assessment of a dental condition based on the one or more dental scans;
    wherein the graphical user interface is configured to provide visual, textual, and/or audio guidance to aid the one or more patients in capturing the one or more dental scans, wherein the visual guidance comprises one or more visual markings or guides indicating a position or an orientation of one or more dental features or regions of interest, and wherein the one or more dental scans are automatically captured when one or more teeth of the one or more patients are aligned with the one or more visual markings or guides.

2. The method of claim 1, wherein the caregiver comprises a dentist, an orthodontist, an oral surgeon, a dental staff practitioner, or an individual having one or more dental specialties.

3. The method of claim 1, wherein the plurality of images are derived from one or more frames of the one or more intraoral videos.

4. The method of claim 1, wherein the plurality of images comprise a plurality of intraoral images of one or more intraoral regions of the patient.

5. The method of claim 1, wherein the graphical user interface is configured to provide the one or more patients with a patient-specific treatment timeline comprising one or more customized treatment milestones and dates.

6. The method of claim 5, wherein the graphical user interface is configured to prompt the one or more patients to capture the one or more dental scans on or before the one or more treatment milestones and dates.

7. The method of claim 5, wherein the patient-specific timeline is configured to display a plurality of dental scans captured by a patient for each treatment milestone and date.

8. The method of claim 1, wherein the one or more dental scans are captured using one or more cameras of a mobile device.

9. The method of claim 8, wherein the mobile device is coupled to an intraoral adapter comprising a viewing channel for capturing the one or more dental scans.

10. The method of claim 9, wherein the viewing channel defines a dental imaging region in which one or more dental features or intraoral regions are visible or present.

11. The method of claim 1, wherein the patient portal comprises a chat user interface that is configured to facilitate remote communication between the one or more patients and the caregiver, and wherein the patient portal is configured to display the one or more dental scans captured by the one or more patients to enable viewing of and access to the dental scans by the caregiver and the one or more patients while chatting.

12. The method of claim 1, further comprising:
providing a caregiver portal for the caregiver to remotely monitor a dental condition of the one or more patients, wherein the caregiver portal comprises an additional graphical user interface that is configured to display the one or more dental scans captured by the one or more patients.

13. The method of claim 12, wherein the caregiver portal comprises a task board interface configured to provide the caregiver with information on one or more tasks associated with incoming patients, current patients, and preparation for dental treatment of the incoming patients or the current patients.

14. The method of claim 12, wherein the caregiver portal comprises a chat user interface that is configured to facilitate remote communication between the caregiver and the patient.

15. The method of claim 14, wherein the caregiver portal is configured to display the one or more dental scans captured by the one or more patients to enable viewing of and access to the dental scans by the caregiver and the one or more patients while chatting.

16. A computer-implemented method for remote dental monitoring, the method comprising:
(a) providing a patient portal for one or more patients to remotely communicate with a caregiver, wherein the patient portal comprises a graphical user interface that is configured to aid the one or more patients in capturing one or more dental scans, wherein the one or more dental scans comprise (i) one or more intraoral videos and (ii) a plurality of images derived from the one or more intraoral videos; and
(b) providing the one or more dental scans to the caregiver for an assessment of a dental condition based on the one or more dental scans,
wherein the graphical user interface is configured to provide the one or more patients with a patient-specific treatment timeline comprising one or more customized treatment milestones and dates, wherein the treatment milestones and dates are determined or influenced in part by one or more factors including an aligner replacement schedule, wherein the aligner replacement schedule is associated with a plurality of trays containing a set of aligners that are designed to be worn by the one or more patients in a sequence, and wherein the plurality of trays are provided to the one or more patients in a pre-locked state.

17. The method of claim 16, wherein unlocking of one or more of the trays is contingent upon the one or more patients successfully completing one or more of the customized treatment milestones, and wherein a code is generated upon successful completion of a particular treatment milestone by the one or more patients, wherein the code is useable or scannable to unlock a tray containing a new aligner to be worn by the one or more patients.

* * * * *